United States Patent
Rey

(10) Patent No.: US 9,399,769 B2
(45) Date of Patent: Jul. 26, 2016

(54) POLYPEPTIDES HAVING CARBOXYPEPTIDASE ACTIVITY AND POLYNUCLEOTIDES ENCODING SAME

(71) Applicant: Novozymes, Inc., Davis, CA (US)

(72) Inventor: Michael Rey, Davis, CA (US)

(73) Assignee: Novozymes, Inc., Davis, CA (US)

( * ) Notice: Subject to any disclaimer, the term of this patent is extended or adjusted under 35 U.S.C. 154(b) by 118 days.

(21) Appl. No.: 14/104,809

(22) Filed: Dec. 12, 2013

(65) Prior Publication Data

US 2014/0106400 A1 Apr. 17, 2014

Related U.S. Application Data

(62) Division of application No. 13/131,738, filed as application No. PCT/US2009/067103 on Dec. 8, 2009, now Pat. No. 8,633,030.

(60) Provisional application No. 61/122,863, filed on Dec. 16, 2008.

(51) Int. Cl.
*C12P 21/06* (2006.01)
*C12N 9/48* (2006.01)
*C12N 9/58* (2006.01)
*C12R 1/645* (2006.01)

(52) U.S. Cl.
CPC *C12N 9/485* (2013.01); *C12N 9/58* (2013.01); *C12P 21/06* (2013.01); *C12R 1/645* (2013.01); *Y02P 20/52* (2015.11)

(58) Field of Classification Search
None
See application file for complete search history.

(56) References Cited

U.S. PATENT DOCUMENTS 7,323,327 B2 * 1/2008 Edens et al. ............... 435/225

FOREIGN PATENT DOCUMENTS

| WO | 9425580 | 11/1994 |
|---|---|---|
| WO | 9609397 | 3/1996 |
| WO | 9814599 | 4/1998 |
| WO | 0177315 | 10/2001 |

OTHER PUBLICATIONS

Rey 2003, Appl Biochem Biotechnol 111, 153-166.
Maheshwari 2000, Microbio Mol Bio Revs 64 (3), 461-488.
Nakadai et al 1972, Agric Biol Chem 36, 1343-1352.
Nakadai et al 1972, Agric Biol Chem 36, 1473-1480.
Nakadai et al 1972, Agric Biol Chem 36, 1481-1488.
Nakadai et al 1973, Agric Biol Chem 37, 1237-1251.
Tekeuchi et al 1982, Curr Microbiol 7, 19-23.
Tekeuchi et al 1986, Agric Biol Chem 50 (3), 633-638.
Lucas et al., 2009, EMBL Access No. GR256997.
Lucas et al., 2009, EMBL Access No. GR256998.
Lucas et al., 2009, EMBL Access No. GR270752.
Sweigard et al, 2008, EMBL Access No. ET456858.
Sweigard et al, 2008, EMBL Access No. ET556097.
Azarenkova et al 1976, Biokhimiya 41, 20-27.
Ichishima et al 1972, J Biochem 72, 1045-1048.
Kim et al, 2005, J Microbiol. 43, 237-243.
TOPO TA Cloning, 1999, Cloning, Invitrogen Corp, 1-21.

* cited by examiner

*Primary Examiner* — Jason Deveau Rosen
(74) *Attorney, Agent, or Firm* — Robert Starnes

(57) ABSTRACT

The present invention relates to isolated polypeptides having carboxypeptidase activity and isolated polynucleotides encoding the polypeptides. The invention also relates to nucleic acid constructs, vectors, and host cells comprising the polynucleotides as well as methods of producing and using the polypeptides.

27 Claims, 3 Drawing Sheets

```
   1  TCCTCCTCGTTTTTGTCTCCATTTCTTCGCCGTCTCCATGACCGCCGCCGGCATTGTTAG
  61  GTAGCCGGCAACTCCTCTCACTCTTTCGACCCGTATCATTTCCACCCTCTCAACCCTACC
                                                              M  A  P  R·
 121  TAACCTGTTGCTTCCGAACCGGCGCGCAAACTGCCAACGGCCATCCACCATGGCCCTCG
       ·R  S  P  T  G  W  L  R  L  P  A  L  I  A  A  V  A  L  P  W·
 181  TCGGTCGCCGACAGGCTGGTTGCGCCTGCCTGCCCTCATCGCGGCCGTCGCTCTCCCGTG
       ·I  I  P  L  A  A  A  D  K  T  A  A  D  Y  F  V  H  S  L  P·
 241  GATAATACCGCTGGCTGCCGCCGACAAGACGGCCGCTGACTATTTTGTCCATTCGCTTCC
       ·G  A  P  E  A  P  P  V  K  M  H  A  C  H  I  E  I  T  P  E·
 301  AGGCGCACCCGAAGCGCCTCCCGTGAAGATGCACGCCGGACACATCGAGATCACCCCCGA
       ·H  N  G  N  I  F  F  W  H  F  Q  N  Q  H  I  A  N  K  Q  R·
 361  ACACAATGGCAACATCTTCTTCTGGCATTTCCAGAACCAGCATATCGCGAACAAGCAGCG
       ·T  V  I  W  L  N  G  G  P  G  C  S  S  E  D  G  A  V  M  E·
 421  GACCGTGATCTGGCTGAACGGCGGGCCGGGCTGCAGCTCCGAGGATGGTGCGGTAATGGA
       ·I  G  P  Y  R  V  K  D  D  K  T  L  V  Y  N  E  G  A  W  N·
 481  GATTGGCCCCTACCGGGTAAAGGATGACAAGACTCTGGTCTACAACGAGGGCGCCTGGAA
       ·E  F  A  N  V  M  F  V  D  N  P  V  G  T  G  Y  S  Y  V  D·
 541  CGAGTTTGCCAACGTCATGTTCGTCGACAATCCCGTCGGCACCGGCTACAGCTATCTCGA
       ·T  N  A  Y  L  H  E  L  D  E  M  A  D  Q  F  V  I  F  L  E·
 601  CACCAACGCCTACTTGCACGAGCTCGACGAGATGGCCGACCAGTTCGTCATCTTCCTGGA
       ·K  W  Y  A  L  F  P  E  Y  E  H  D  D  L  Y  I  A  G  E  S·
 661  GAAGTGGTATGCTCTGTTCCCAGAGTACGAACACGACGATCTCTACATCGCCGGAGAGTC
       ·Y  A  G  Q  Y  I  P  Y  I  A  K  H  I  L  D  R  N  K  L  P·
 721  ATACGCTGGCCAGTACATCCCGTACATCGCGAAGCACATTCTCGACCGTAACAAGCTTCC
       ·T  T  K  H  K  W  N  L  M  G  L  L  I  G  N  W  I  S  P·
 781  GACGACGAAGCACAAGTGGAACCTGATGGGCCTCCTCATCGGCAACGGATGGATCTCGCC
       ·P  E  Q  Y  E  A  Y  L  Q  Y  A  F  D  R  G  L  V  Q  K  G·
 841  GCCCGAGCAGTACGAAGCCTACCTCCAATACGCCTTCGACAGGGGCCTTGTGCAGAAGGG
       ·S  D  I  G  N  K  L  E  V  Q  Q  R  I  C  Q  K  Q  L  A  V·
 901  CAGTGACATCGGCAACAAACTCGAGGTCCAGCAACGCATTTGCCAGAAGCAGCTGGCCGT
       ·S  K  G  A  V  D  S  P  D  C  E  K  I  L  Q  D  L  L  R  F·
 961  CAGCAAGGGCGCCGTCGATAGCCCGGACTGCGAAAAGATCCTCCAGGATCTTCTGCGGTT
       ·T  A  T  P  G  K  D  G  Q  L  E  C  Y  N  M  Y  D  V  R  L·
1021  CACCGCTACTCCCGGCAAGGACGGCCAACTCGAATGCTACAACATGTACGACGTGCGCCT
       ·K  D  T  Y  P  S  C  G  M  N  W  P  P  D  L  A  H  V  T  P·
1081  CAAAGACACTTACCCATCCTGCGGCATGAACTGGCCGCCCGATCTGGCTCACGTCACCCC
       ·Y  L  R  Q  K  E  V  V  E  A  L  H  V  N  P  N  K  V  T  G·
1141  GTACCTTCGCCAGAAGGAAGTCGTCGAAGCCCTCCACGTCAACCCGAACAAGGTCACCGG
       ·W  V  E  C  N  G  Q  V  G  Q  S  F  K  P  V  N  S  K  P  S·
1201  CTGGGTGGAATGCAACGGCCAGGTGGGCCAGAGCTTCAAGCCCGTCAACTCGAAGCCCTC
       ·I  D  I  L  P  D  I  L  A  E  I  P  V  I  L  F  S  G  S  E·
1261  GATCGACATCCTCCCGGACATCCTGGCCGAGATACCCGTCATCCTCTTCTCCGGCTCCGA
       ·D  L  I  C  N  H  L  G  T  E  A  F  I  S  N  M  A  W  N  G·
1321  AGACCTCATCTGCAACCACCTCGGCACCGAGGCGTTCATCAGCAACATGGCGTGGAACGG
       ·G  R  G  F  E  L  S  P  G  T  W  A  P  R  R  E  W  T  F  E·
1381  CGGCCGCGGCTTCGAGCTGTCGCCCGGCACCTGGGCGCCGCGCCGGGAATGGACCTTCGA
       ·G  E  P  A  G  F  W  Q  E  A  R  N  L  T  Y  V  V  F  Y  N·
1441  GGGCGAACCTGCCGGCTTCTGGCAGGAGGCGCGCAACCTCACCTACGTGGTCTTCTACAA
       ·S  S  H  M  V  P  F  D  H  P  R  R  T  R  D  M  L  D  R  F·
1501  CAGCAGCCACATGGTGCCGTTCGACCACCCGCGCCGCACGCGCGACATGCTCGACCGCTT
```

Fig. 1A

```
              · M   G   V   D   I   S   S   I   G   G   K   P   T   D   S   R   L   D   G   E ·
       1561   CATGGGCGTCGACATCAGCTCCATCGGTGGCAAGCCGACCGACAGCCGCCTCGACGGCGA
              · K   G   P   E   T   T   V   G   G   A   A   G   N   G   T   A   A   Q   E   A ·
       1621   GAAGGGACCCGAGACCACGGTCGGCGGCGCCGCGGGCAACGGCACTGCCGCCCAGGAGGC
              · E   K   A   K   L   D   A   A   K   W   E   A   Y   R   R   S   G   E   I   V ·
       1681   CGAGAAGGCCAAGCTCGACGCCGCCAAGTGGGAGGCCTACCGCCGCTCGGGCGAGATCGT
              · L   V   I   V   A   V   A   A   A   A   W   G   Y   F   V   W   R   D   R   R ·
       1741   GCTCGTCATCGTCGCCGTCGCCGCCGCCGCCTGGGGCTACTTCGTCTGGCGCGACCGCCG
              · R   R   Q   G   Y   Q   G   L   A   D   G   P   G   R   A   A   G   S   S   S ·
       1801   CAGGAGGCAGGGCTACCAGGGCCTGGCCGACGGGCCCGGCCGGGCCGCCGGCTCCTCCAG
              · S   S   E   R   L   E   T   F   R   T   Q   R   T   L   R   R   D   R   D   L ·
       1861   CTCGTCTGAGCGCCTCGAGACCTTCCGCACCCAGCGCACCTTGCGCAGGGACAGGGATCT
              · E   A   G   D   F   D   E   N   Q   L   D   S   L   H   V   R   S   P   A   E ·
       1921   GGAGGCCGGCGATTTCGACGAGAACCAGCTGGATTCGCTGCACGTCCGGTCGCCCGCCGA
              · E   Q   A   D   A   R   Y   S   L   G   G   E   E   S   E   D   D   E   E   E ·
       1981   GGAGCAGGCTGATGCGAGGTACAGCCTGGGAGGGGAAGAAAGCGAGGATGACGAGGAGGA
              · G   T   T   K   K   G   G   K   R   R   E   K   A   A   K   A   G   E   S   S ·
       2041   AGGGACGACGAAAAAGGGCGGGAAAAGAAGGGAGAAGGCGGCAAAAGCCGGGGAAAGTTC
              · S
       2101   ATGATCCGCCCGGATTGGGTTCGACAGAGCGTTTTGAAAGTGAGGCATACACAGCACGTA
       2161   CATACATACATCCATGGGTCGTCTTGTAGATTGTTGGTATGGTCGGGATGGCGTCAGCGG
       2221   TAACTGTATTTTCTGGTCCTGTTGGTTTCTTGTGCTATTGTGGCTCAGCTGATGGGAAT
       2281   GAGAAACACGCTACATGCAAAAAAAAAAAAAAAAAAAAAAAAAAAAAAAAAA
```

Fig. 1B

SEQUENCE LISTING

```
<160> NUMBER OF SEQ ID NOS: 3

<210> SEQ ID NO 1
<211> LENGTH: 2332
<212> TYPE: DNA
<213> ORGANISM: Thielavia terrestris

<400> SEQUENCE: 1
tcctcctcgt ttttgtctcc atttcttcgc cgtctccatg accgccgccg gcattgttag      60
gtagccggca actcctctca ctctttcgac ccgtatcatt tccaccctct caaccctacc     120
taacctgttg cttccgaacc ggcgcgcaaa ctgccaacgg ccatccacca tggcccctcg     180
tcggtcgccg acaggctggt tgcgcctgcc tgccctcatc gcggccgtcg ctctcccgtg     240
gataataccg ctggctgccg ccgacaagac ggccgctgac tattttgtcc attcgcttcc     300
aggcgcaccc gaagcgcctc ccgtgaagat gcacgccgga cacatcgaga tcaccccccga    360 acacaatggc aacatcttct tctggcatt ccagaaccag catatcgcga caagcagcg       420 gaccgtgatc tggctgaacg gcgggccggg ctgcagctcc gaggatggtg cggtaatgga     480
gattggcccc taccgggtaa aggatgacaa gactctggtc tacaacgagg gcgcctggaa     540
cgagtttgcg aacgtcatgt tcgtcgacaa tcccgtcggc accggctaca gctatgtcga     600
caccaacgcc tacttgcacg agctcgacga gatggccgac cagttcgtca tcttcctgga     660
gaagtggtat gctctgttcc cagagtacga acacgacgat ctctacatcg ccggagagtc     720
atacgctggc cagtacatcc cgtacatcgc gaagcacatt ctcgaccgta acaagcttcc     780
gacgacgaag cacaagtgga acctgatggg cctcctcatc ggcaacggat ggatctcgcc     840
gcccgagcag tacgaagcct acctccaata cgccttcgac aggggccttg tgcagaaggg     900
cagtgacatc ggcaacaaac tcgaggtcca gcaacgcatt tgccagaagc agctggccgt     960
cagcaagggc gccgtcgata gcccggactg cgaaaagatc ctccaggatc ttctgcggtt    1020
```

```
caccgctact cccggcaagg acggccaact cgaatgctac aacatgtacg acgtgcgcct   1080
caaagacact tacccatcct gcggcatgaa ctggccgccc gatctggctc acgtcacccc   1140
gtaccttcgc cagaaggaag tcgtcgaagc cctccacgtc aacccgaaca aggtcaccgg   1200
ctgggtggaa tgcaacggcc aggtgggcca gagcttcaag cccgtcaact cgaagccctc   1260
gatcgacatc ctcccggaca tcctggccga gatacccgtc atcctcttct ccggctccga   1320
agacctcatc tgcaaccacc tcggcaccga ggcgttcatc agcaacatgg cgtggaacgg   1380
cggccgcggc ttcgagctgt cgcccggcac ctgggcgccg cgccgggaat ggaccttcga   1440
gggcgaacct gccggcttct ggcaggaggc gcgcaacctc acctacgtgg tcttctacaa   1500
cagcagccac atggtgccgt cgaccacccg cgccgcacg cgcgacatgc tcgaccgctt   1560
catgggcgtc gacatcagct ccatcggtgg caagccgacc gacagccgcc tcgacgcgca   1620
gaagggaccc gagaccacgg tcggcggcgc cgcgggcaac ggcactgccg cccaggaggc   1680
cgagaaggcc aagctcgacg ccgccaagtg ggaggcctac cgccgctcgg gcgagatcgt   1740
gctcgtcatc gtcgccgtcg ccgccgccgc ctggggctac ttcgtctggc gcgaccgccg   1800
caggaggcag ggctaccagg gcctggccga cgggcccggc cgggccgccg gctcctccag   1860
ctcgtctgag cgcctcgaga ccttccgcac ccagcgcacc ttgcgcaggg acagggatct   1920
ggaggccggc gatttcgacg agaaccagct ggattcgctg cacgtccggt cgcccgccga   1980
ggagcaggct gatgcgaggt acagcctggg aggggaagaa agcgaggatg acgaggagga   2040
agggacgacg aaaaagggcg ggaaaagaag ggagaaggcg gcaaaagccg gggaaagttc   2100
atgatccgcc cggattgggt tcgacagagc gttttgaaag tgaggcatac acagcacgta   2160
catacataca tccatgggtc gtcttgtaga ttgttggtat ggtcgggatg gcgtcagcgg   2220
taactgtatt ttctggtcct gttggttttc ttgtgctatt gtggctcagc tgatgggaat   2280
gagaaacacg ctacatgcaa aaaaaaaaaa aaaaaaaaa aaaaaaaaa aa             2332
```

<210> SEQ ID NO 2
<211> LENGTH: 645
<212> TYPE: PRT
<213> ORGANISM: Thielavia terrestris

<400> SEQUENCE: 2

Met Ala Pro Arg Arg Ser Pro Thr Gly Trp Leu Arg Leu Pro Ala Leu
1               5                   10                  15

Ile Ala Ala Val Ala Leu Pro Trp Ile Ile Pro Leu Ala Ala Ala Asp
            20                  25                  30

Lys Thr Ala Ala Asp Tyr Phe Val His Ser Leu Pro Gly Ala Pro Glu
        35                  40                  45

Ala Pro Val Lys Met His Ala Gly His Ile Glu Ile Thr Pro Glu
    50                  55                  60

His Asn Gly Asn Ile Phe Phe Trp His Phe Gln Asn Gln His Ile Ala
65                  70                  75                  80

Asn Lys Gln Arg Thr Val Ile Trp Leu Asn Gly Gly Pro Gly Cys Ser
                85                  90                  95

Ser Glu Asp Gly Ala Val Met Glu Ile Gly Pro Tyr Arg Val Lys Asp
            100                 105                 110

Asp Lys Thr Leu Val Tyr Asn Glu Gly Ala Trp Asn Glu Phe Ala Asn
        115                 120                 125

Val Met Phe Val Asp Asn Pro Val Gly Thr Gly Tyr Ser Tyr Val Asp
    130                 135                 140

```
Thr Asn Ala Tyr Leu His Glu Leu Asp Glu Met Ala Asp Gln Phe Val
145                 150                 155                 160

Ile Phe Leu Glu Lys Trp Tyr Ala Leu Phe Pro Glu Tyr Glu His Asp
                165                 170                 175

Asp Leu Tyr Ile Ala Gly Glu Ser Tyr Ala Gly Gln Tyr Ile Pro Tyr
            180                 185                 190

Ile Ala Lys His Ile Leu Asp Arg Asn Lys Leu Pro Thr Thr Lys His
        195                 200                 205

Lys Trp Asn Leu Met Gly Leu Leu Ile Gly Asn Gly Trp Ile Ser Pro
    210                 215                 220

Pro Glu Gln Tyr Glu Ala Tyr Leu Gln Tyr Ala Phe Arg Gly Leu
225                 230                 235                 240

Val Gln Lys Gly Ser Asp Ile Gly Asn Lys Leu Glu Val Gln Gln Arg
                245                 250                 255

Ile Cys Gln Lys Gln Leu Ala Val Ser Lys Gly Ala Val Asp Ser Pro
            260                 265                 270

Asp Cys Glu Lys Ile Leu Gln Asp Leu Leu Arg Phe Thr Ala Thr Pro
        275                 280                 285

Gly Lys Asp Gly Gln Leu Glu Cys Tyr Asn Met Tyr Asp Val Arg Leu
    290                 295                 300

Lys Asp Thr Tyr Pro Ser Cys Gly Met Asn Trp Pro Pro Asp Leu Ala
305                 310                 315                 320

His Val Thr Pro Tyr Leu Arg Gln Lys Glu Val Val Glu Ala Leu His
                325                 330                 335

Val Asn Pro Asn Lys Val Thr Gly Trp Val Glu Cys Asn Gly Gln Val
            340                 345                 350

Gly Gln Ser Phe Lys Pro Val Asn Ser Lys Pro Ser Ile Asp Ile Leu
        355                 360                 365

Pro Asp Ile Leu Ala Glu Ile Pro Val Ile Leu Phe Ser Gly Ser Glu
    370                 375                 380

Asp Leu Ile Cys Asn His Leu Gly Thr Glu Ala Phe Ile Ser Asn Met
385                 390                 395                 400

Ala Trp Asn Gly Gly Arg Gly Phe Glu Leu Ser Pro Gly Thr Trp Ala
                405                 410                 415

Pro Arg Arg Glu Trp Thr Phe Glu Gly Glu Pro Ala Gly Phe Trp Gln
            420                 425                 430

Glu Ala Arg Asn Leu Thr Tyr Val Val Phe Tyr Asn Ser Ser His Met
        435                 440                 445

Val Pro Phe Asp His Pro Arg Arg Thr Arg Asp Met Leu Asp Arg Phe
    450                 455                 460

Met Gly Val Asp Ile Ser Ser Ile Gly Gly Lys Pro Thr Asp Ser Arg
465                 470                 475                 480

Leu Asp Gly Glu Lys Gly Pro Glu Thr Thr Val Gly Gly Ala Ala Gly
                485                 490                 495

Asn Gly Thr Ala Ala Gln Glu Ala Glu Lys Ala Lys Leu Asp Ala Ala
            500                 505                 510

Lys Trp Glu Ala Tyr Arg Arg Ser Gly Glu Ile Val Leu Val Ile Val
        515                 520                 525

Ala Val Ala Ala Ala Trp Gly Tyr Phe Val Trp Arg Asp Arg Arg
    530                 535                 540

Arg Arg Gln Gly Tyr Gln Gly Leu Ala Asp Gly Pro Gly Arg Ala Ala
545                 550                 555                 560
```

-continued

```
Gly Ser Ser Ser Ser Ser Glu Arg Leu Glu Thr Phe Arg Thr Gln Arg
                565             570              575

Thr Leu Arg Arg Asp Arg Asp Leu Glu Ala Gly Asp Phe Asp Glu Asn
            580             585              590

Gln Leu Asp Ser Leu His Val Arg Ser Pro Ala Glu Glu Gln Ala Asp
        595             600             605

Ala Arg Tyr Ser Leu Gly Gly Glu Glu Ser Glu Asp Asp Glu Glu Glu
    610             615             620

Gly Thr Thr Lys Lys Gly Gly Lys Arg Arg Glu Lys Ala Ala Lys Ala
625             630             635             640

Gly Glu Ser Ser Ser
                645

<210> SEQ ID NO 3
<211> LENGTH: 16
<212> TYPE: DNA
<213> ORGANISM: Artificial
<220> FEATURE:
<223> OTHER INFORMATION: artificial primer

<400> SEQUENCE: 3
gtaaaacgac ggccag                                                         16
```

POLYPEPTIDES HAVING CARBOXYPEPTIDASE ACTIVITY AND POLYNUCLEOTIDES ENCODING SAME

CROSS-REFERENCE TO RELATED APPLICATIONS

This application is a divisional application of U.S. patent application Ser. No. 13/131,738 filed on Jul. 25, 2011, now U.S. Pat. No. 8,633,030, which is a 35 U.S.C. 371 national application of PCT/US 2009/067103 filed on Dec. 8, 2009 and claims priority from U.S. provisional application Ser. No. 61/122,863 filed on Dec 16, 2008, which applications are fully incorporated herein by reference.

REFERENCE TO A SEQUENCE LISTING

This application contains a Sequence Listing filed electronically by EFS, which is incorporated herein by reference.

REFERENCE TO A DEPOSIT OF BIOLOGICAL MATERIAL

This application contains a reference to a deposit of biological material, which deposit is incorporated herein by reference.

BACKGROUND OF THE INVENTION

1. Field of the Invention

The present invention relates to isolated polypeptides having carboxypeptidase activity and isolated polynucleotides encoding the polypeptides. The invention also relates to nucleic acid constructs, vectors, and host cells comprising the polynucleotides as well as methods of producing and using the polypeptides.

2. Description of the Related Art

Various food products, e.g., soups, sauces and seasonings, contain flavoring agents obtained by hydrolysis of proteinaceous materials. This hydrolysis is conventionally accomplished using strong hydrochloric acid, followed by neutralization with sodium hydroxide. However, such chemical hydrolysis leads to severe degradation of the amino acids obtained during the hydrolysis, and also to hazardous byproducts formed in the course of this chemical reaction. Increasing concern over the use of flavoring agents obtained by chemical hydrolysis has led to the development of enzymatic hydrolysis processes.

Enzymatic hydrolysis processes aim at obtaining a high degree of hydrolysis (DH), and this is usually attained using a complex of unspecific acting proteolytic enzymes (i.e., unspecific acting endo- and exo-peptidases). For example, WO 94/25580 describes a method for hydrolyzing proteins by use of an unspecific acting enzyme preparation obtained from *Aspergillus oryzae*. Specific acting proteolytic enzymes have not been used for this purpose because such enzymes only lead to an inadequate degree of hydrolysis.

Acid carboxypeptidases (EC 3.4.16) are serine exopeptidases which catalyze the removal of amino acids from the C-terminus of peptides, oligopeptides or proteins. These carboxypeptidases generally have a narrow substrate specificity, i.e., they can cleave only few amino acids.

Acid carboxypeptidases of *Aspergillus oryzae* have been reported previously. For instance, Nakadai, Nasuno, and Iguchi, 1972, *Agricultural and Biological Chemistry* 36: 1343-1352, disclose a carboxypeptidase I with a molecular weight of 120 kDa (gel filtration) and optimal activity in the pH range 3.0 to 4.0. Nakadai, Nasuno, and Iguchi, 1972, *Agricultural and Biological Chemistry* 36: 1473-1480, disclose a carboxypeptidase II with a molecular weight of 105 kDa (gel filtration) and optimal activity at pH 3.0. Nakadai, Nasuno, and Iguchi, 1972, *Agricultural and Biological Chemistry* 36: 1481-1488, disclose a carboxypeptidase III with a molecular weight of 61 kDa (gel filtration) and a pH optimum of 3.0. Nakadai, Nasuno, and Iguchi, 1972, *Agricultural and Biological Chemistry* 37: 1237-1251, disclose a carboxypeptidase IV with a molecular weight of 43 kDa (gel filtration) and optimal activity at pH 3.0. Tekeuchi and Ichishima, 1986, *Agricultural and Biological Chemistry* 50: 633-638, disclose a carboxypeptidase O with a molecular weight of 73 kDa (SDS-PAGE). Tekeuchi, Ushijima, and Ichishima, 1982, *Current Microbiology* 7: 19-23, disclose a carboxypeptidase O-1 and a carboxypeptidase O-2 both with a molecular weight of 63 kDa (gel filtration) and optimal activity at a pH in the range of 3.7 to 4.0. Ichishima et al., 1972, *Journal of Biochemistry* 72: 1045-1048, disclose a comparison of the enzymatic properties of several *Aspergillus* acid carboxypeptidases. Azarenkova et al., 1976, *Biokhimiya* 41: 20-27, disclose the isolation of an acid carboxypeptidase from *Aspergillus oryzae* with a molecular weight of 37 kDa (SDS-PAGE) and a pH optimum of 4 to 5.

The production of protein hydrolysates with desirable organoleptic properties and high degrees of hydrolysis generally requires the use of a mixture of peptidase activities. It would be desirable to provide a single component peptidase enzyme having activity useful for improving the organoleptic properties and degree of hydrolysis of protein hydrolysates used in food products either alone or in combination with other enzymes.

The present invention provides polypeptides having carboxypeptidase activity and polynucleotides encoding the polypeptides.

SUMMARY OF THE INVENTION

The present invention relates to isolated polypeptides having carboxypeptidase activity selected from the group consisting of:

(a) a polypeptide comprising an amino acid sequence having at least 80% sequence identity to the mature polypeptide of SEQ ID NO: 2;

(b) a polypeptide encoded by a polynucleotide that hybridizes under at least high stringency conditions with (i) the mature polypeptide coding sequence of SEQ ID NO: 1, (ii) the genomic DNA sequence comprising the mature polypeptide coding sequence of SEQ ID NO: 1, or (iii) a full-length complementary strand of (i) or (ii);

(c) a polypeptide encoded by a polynucleotide comprising a nucleotide sequence having at least 80% sequence identity to the mature polypeptide coding sequence of SEQ ID NO: 1; and (d) a variant comprising a substitution, deletion, and/or insertion of one or more (several) amino acids of the mature polypeptide of SEQ ID NO: 2.

The present invention also relates to isolated polynucleotides encoding polypeptides having carboxypeptidase activity, selected from the group consisting of:

(a) a polynucleotide encoding a polypeptide comprising an amino acid sequence having at least 80% sequence identity to the mature polypeptide of SEQ ID NO: 2;

(b) a polynucleotide that hybridizes under at least high stringency conditions with (i) the mature polypeptide coding sequence of SEQ ID NO: 1, (ii) the genomic DNA sequence comprising the mature polypeptide coding sequence of SEQ ID NO: 1, or (iii) a full-length complementary strand of (i) or (ii);

(c) a polynucleotide comprising a nucleotide sequence having at least 80% sequence identity to the mature polypeptide coding sequence of SEQ ID NO: 1; and (d) a polynucleotide encoding a variant comprising a substitution, deletion, and/or insertion of one or more (several) amino acids of the mature polypeptide of SEQ ID NO: 2.

The present invention also relates to nucleic acid constructs, recombinant expression vectors, and recombinant host cells comprising the polynucleotides, and to methods of producing the polypeptides having carboxypeptidase activity.

The present invention also relates to methods of inhibiting the expression of a polypeptide having carboxypeptidase activity in a cell, comprising administering to the cell or expressing in the cell a double-stranded RNA (dsRNA) molecule, wherein the dsRNA comprises a subsequence of a polynucleotide of the present invention. The present also relates to such a double-stranded inhibitory RNA (dsRNA) molecule, wherein optionally the dsRNA is a siRNA or a miRNA molecule.

The present invention also relates to methods of obtaining hydrolysates from proteinaceous substrates which comprise subjecting the proteinaceous material to a polypeptide with carboxypeptidase activity alone or in combination with an endopeptidase, and to hydrolysates obtained from the method.

The present invention also relates to methods of obtaining from a proteinaceous substrate a hydrolysate enriched in free glutamic acid and/or peptide bound glutamic acid residues, which methods comprise subjecting the substrate to a deamidation process and to the action of a polypeptide having carboxypeptidase activity.

The present invention further relates to flavor-improving compositions comprising a polypeptide with carboxypeptidase activity. The compositions may further comprise additional enzymatic activities.

The present invention also relates to plants comprising an isolated polynucleotide encoding a polypeptide having carboxypeptidase activity.

The present invention also relates to methods of producing a polypeptide having carboxypeptidase activity, comprising: (a) cultivating a transgenic plant or a plant cell comprising a polynucleotide encoding the polypeptide having carboxypeptidase activity under conditions conducive for production of the polypeptide; and (b) recovering the polypeptide.

The present invention also relates to an isolated polynucleotide encoding a signal peptide comprising or consisting of amino acids 1 to 31 of SEQ ID NO: 2; to nucleic acid constructs, expression vectors, and recombinant host cells comprising the polynucleotides; and to methods of producing a protein.

BRIEF DESCRIPTION OF THE FIGURES

FIGS. 1A and 1B show the cDNA sequence and the deduced amino acid sequence of a *Thielavia terrestris* NRRL 8126 carboxypeptidase gene (SEQ ID NOs: 1 and 2, respectively).

DEFINITIONS

Figure 2:
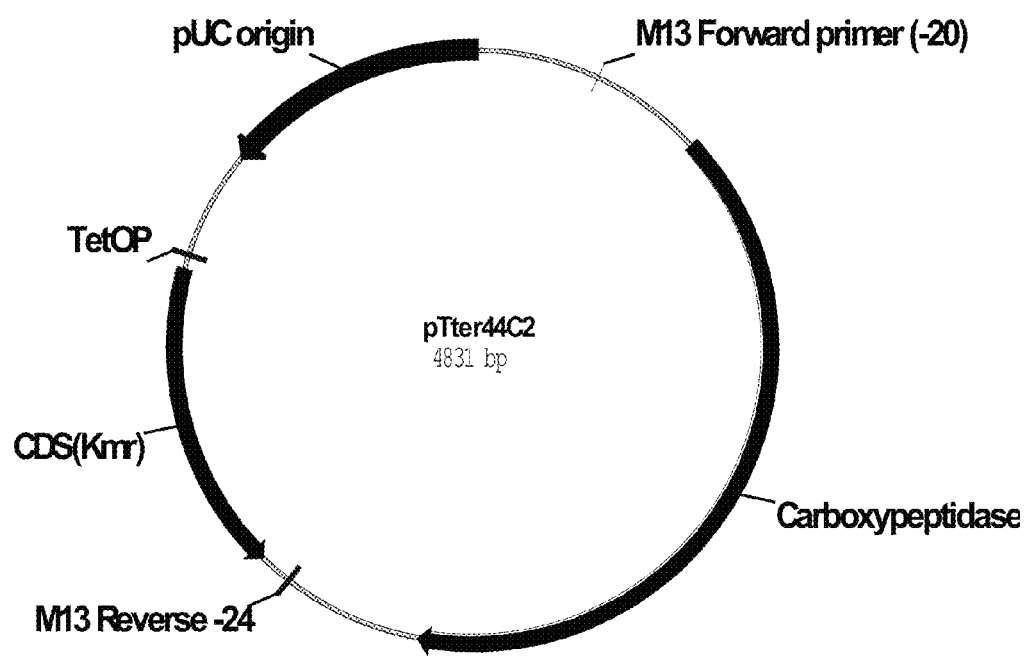
FIG. 2 shows a map of pTter44C2.

Carboxypeptidase activity: The term "carboxypeptidase activity" is defined herein as a serine-type carboxypeptidase activity (EC 3.4.16) that catalyzes the removal of amino acids from the C-terminus of peptides, oligopeptides or proteins. Defined in a general manner, the carboxypeptidase activity is capable of cleaving amino acid X from the C-terminus of a peptide, polypeptide, or protein, wherein X represents any amino acid residue selected from the group consisting of Ala, Arg, Asn, Asp, Cys, Gln, Glu, Gly, His, Ile, Leu, Lys, Met, Phe, Pro, Ser, Thr, Trp, Tyr, and Val. It will be understood that the isolated polypeptides having carboxypeptidase activity of the present invention are unspecific as to the amino acid sequence of the peptide, polypeptide, or protein to be cleaved. Carboxypeptidase activity can be measured according to the procedures described in WO 1998/014599. One unit of carboxypeptidase activity equals the amount of enzyme capable of releasing 1 μmole of amino acid per minute under optimal conditions of pH and temperature.

The polypeptides of the present invention have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the carboxypeptidase activity of the mature polypeptide of SEQ ID NO: 2.

Isolated polypeptide: The term "isolated polypeptide" as used herein refers to a polypeptide that is isolated from a source. In a preferred aspect, the polypeptide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by SDS-PAGE.

Substantially pure polypeptide: The term "substantially pure polypeptide" denotes herein a polypeptide preparation that contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively or recombinantly associated. It is, therefore, preferred that the substantially pure polypeptide is at least 92% pure, preferably at least 94% pure, more preferably at least 95% pure, more preferably at least 96% pure, more preferably at least 97% pure, more preferably at least 98% pure, even more preferably at least 99% pure, most preferably at least 99.5% pure, and even most preferably 100% pure by weight of the total polypeptide material present in the preparation. The polypeptides of the present invention are preferably in a substantially pure form, i.e., that the polypeptide preparation is essentially free of other polypeptide material with which it is natively or recombinantly associated. This can be accomplished, for example, by preparing the polypeptide by well-known recombinant methods or by classical purification methods.

Mature polypeptide: The term "mature polypeptide" is defined herein as a polypeptide in its final form following translation and any post-translational modifications, such as N-terminal processing, C-terminal truncation, glycosylation, phosphorylation, etc. In one aspect, the mature polypeptide is amino acids 32 to 645 of SEQ ID NO: 2 based on the SignalP program (Nielsen et al., 1997, *Protein Engineering* 10:1-6) that predicts amino acids 1 to 31 of SEQ ID NO: 2 are a signal peptide.

Mature polypeptide coding sequence: The term "mature polypeptide coding sequence" is defined herein as a nucleotide sequence that encodes a mature polypeptide having carboxypeptidase activity. In one aspect, the mature polypeptide coding sequence is nucleotides 263 to 2104 of SEQ ID NO: 1 based on the SignalP program (Nielsen et al., 1997, supra) that predicts nucleotides 170 to 262 of SEQ ID NO: 1 encode a signal peptide.

Sequence Identity: The relatedness between two amino acid sequences or between two nucleotide sequences is described by the parameter "sequence identity".

For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends in Genetics* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment−Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the —nobrief option) is used as the percent identity and is calculated as follows:

(Identical Deoxyribonucleotides×100)/(Length of Alignment−Total Number of Gaps in Alignment)

Homologous sequence: The term "homologous sequence" is defined herein as a predicted protein having an E value (or expectancy score) of less than 0.001 in a tfasty search (Pearson, W. R., 1999, in *Bioinformatics Methods and Protocols*, S. Misener and S. A. Krawetz, ed., pp. 185-219) with the *Thielavia terrestris* polypeptide having carboxypeptidase activity of SEQ ID NO: 2 or the mature polypeptide thereof.

Polypeptide fragment: The term "polypeptide fragment" is defined herein as a polypeptide having one or more (several) amino acids deleted from the amino and/or carboxyl terminus of the mature polypeptide of SEQ ID NO: 2; or a homologous sequence thereof; wherein the fragment has carboxypeptidase activity. In one aspect, a fragment contains at least 520 amino acid residues, more preferably at least 550 amino acid residues, and most preferably at least 580 amino acid residues of the mature polypeptide of SEQ ID NO: 2 or a homologous sequence thereof.

Subsequence: The term "subsequence" is defined herein as a nucleotide sequence having one or more (several) nucleotides deleted from the 5' and/or 3' end of the mature polypeptide coding sequence of SEQ ID NO: 1; or a homologous sequence thereof; wherein the subsequence encodes a polypeptide fragment having carboxypeptidase activity. In one aspect, a subsequence contains at least 1560 nucleotides, more preferably at least 1650 nucleotides, and most preferably at least 1740 nucleotides of the mature polypeptide coding sequence of SEQ ID NO: 1 or a homologous sequence thereof.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" as used herein refers to a polynucleotide that is isolated from a source. In a preferred aspect, the polynucleotide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by agarose electrophoresis.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively or recombinantly associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99% pure, and even most preferably at least 99.5% pure by weight. The polynucleotides of the present invention are preferably in a substantially pure form, i.e., that the polynucleotide preparation is essentially free of other polynucleotide material with which it is natively or recombinantly associated. The polynucleotides may be of genomic, cDNA, RNA, semisynthetic, synthetic origin, or any combinations thereof.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant nucleotide sequence.

cDNA: The term "cDNA" is defined herein as a DNA molecule that can be prepared by reverse transcription from a mature, spliced, mRNA molecule obtained from a eukaryotic cell. cDNA lacks intron sequences that may be present in the corresponding genomic DNA. The initial, primary RNA transcript is a precursor to mRNA that is processed through a series of steps before appearing as mature spliced mRNA. These steps include the removal of intron sequences by a process called splicing. cDNA derived from mRNA lacks, therefore, any intron sequences.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Control sequences: The term "control sequences" is defined herein to include all components necessary for the expression of a polynucleotide encoding a polypeptide of the present invention. Each control sequence may be native or foreign to the nucleotide sequence encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of a polynucleotide sequence such that the control sequence directs the expression of the coding sequence of a polypeptide.

Expression: The term "expression" includes any step involved in the production of a polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the present invention and is operably linked to additional nucleotides that provide for its expression.

Host cell: The term "host cell", as used herein, includes any cell type that is susceptible to transformation, transfection, transduction, and the like with a nucleic acid construct or expression vector comprising a polynucleotide of the present invention.

Modification: The term "modification" means herein any chemical modification of the polypeptide comprising or consisting of the mature polypeptide of SEQ ID NO: 2; or a homologous sequence thereof; as well as genetic manipulation of the DNA encoding such a polypeptide. The modification can be a substitution, a deletion and/or an insertion of one or more (several) amino acids as well as replacements of one or more (several) amino acid side chains.

Artificial variant: When used herein, the term "artificial variant" means a polypeptide having carboxypeptidase activity produced by an organism expressing a modified polynucleotide sequence of the mature polypeptide coding sequence of SEQ ID NO: 1; or a homologous sequence thereof. The modified nucleotide sequence is obtained through human intervention by modification of the polynucleotide sequence disclosed in SEQ ID NO: 1; or a homologous sequence thereof.

DETAILED DESCRIPTION OF THE INVENTION

Polypeptides Having Carboxypeptidase Activity

In a first aspect, the present invention relates to isolated polypeptides comprising amino acid sequences having a degree of sequence identity to the mature polypeptide of SEQ ID NO: 2 of preferably at least 80%, more preferably at least 85%, more preferably at least 90%, even more preferably at least 95%, and most preferably at least 96%, at least 97%, at least 98%, or at least 99%, which have carboxypeptidase activity (hereinafter "homologous polypeptides"). In a preferred aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 2.

A polypeptide of the present invention preferably comprises the amino acid sequence of SEQ ID NO: 2 or an allelic variant thereof; or a fragment thereof having carboxypeptidase activity. In a preferred aspect, the polypeptide comprises the amino acid sequence of SEQ ID NO: 2. In another preferred aspect, the polypeptide comprises the mature polypeptide of SEQ ID NO: 2. In another preferred aspect, the polypeptide comprises amino acids 32 to 645 of SEQ ID NO: 2, or an allelic variant thereof; or a fragment thereof having carboxypeptidase activity. In another preferred aspect, the polypeptide comprises amino acids 32 to 645 of SEQ ID NO: 2. In another preferred aspect, the polypeptide consists of the amino acid sequence of SEQ ID NO: 2 or an allelic variant thereof; or a fragment thereof having carboxypeptidase activity. In another preferred aspect, the polypeptide consists of the amino acid sequence of SEQ ID NO: 2. In another preferred aspect, the polypeptide consists of the mature polypeptide of SEQ ID NO: 2. In another preferred aspect, the polypeptide consists of amino acids 32 to 645 of SEQ ID NO: 2 or an allelic variant thereof; or a fragment thereof having carboxypeptidase activity. In another preferred aspect, the polypeptide consists of amino acids 32 to 645 of SEQ ID NO: 2.

In a second aspect, the present invention relates to isolated polypeptides having carboxypeptidase activity that are encoded by polynucleotides that hybridize under preferably very low stringency conditions, more preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 1, (ii) the genomic DNA sequence comprising the mature polypeptide coding sequence of SEQ ID NO: 1, or (iii) a full-length complementary strand of (i) or (ii) (J. Sambrook, E. F. Fritsch, and T. Maniatis, 1989, *Molecular Cloning, A Laboratory Manual*, 2d edition, Cold Spring Harbor, N.Y.).

The nucleotide sequence of SEQ ID NO: 1; or a subsequence thereof; as well as the amino acid sequence of SEQ ID NO: 2; or a fragment thereof; may be used to design nucleic acid probes to identify and clone DNA encoding polypeptides having carboxypeptidase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes that are preferably at least 600 nucleotides, more preferably at least 700 nucleotides, even more preferably at least 800 nucleotides, or most preferably at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may, therefore, be screened for DNA that hybridizes with the probes described above and encodes a polypeptide having carboxypeptidase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1, or a subsequence thereof, the carrier material is preferably used in a Southern blot.

For purposes of the present invention, hybridization indicates that the nucleotide sequence hybridizes to a labeled nucleic acid probe corresponding to the mature polypeptide coding sequence of SEQ ID NO: 1; the genomic DNA sequence comprising the mature polypeptide coding sequence of SEQ ID NO: 1; its full-length complementary strand; or a subsequence thereof; under very low to very high stringency conditions. Molecules to which the nucleic acid probe hybridizes under these conditions can be detected using, for example, X-ray film.

In a preferred aspect, the nucleic acid probe is the mature polypeptide coding sequence of SEQ ID NO: 1. In another preferred aspect, the nucleic acid probe is nucleotides 263 to 2104 of SEQ ID NO: 1. In another preferred aspect, the nucleic acid probe is a polynucleotide sequence that encodes the polypeptide of SEQ ID NO: 2, or a subsequence thereof. In another preferred aspect, the nucleic acid probe is SEQ ID NO: 1. In another preferred aspect, the nucleic acid probe is the polynucleotide sequence contained in plasmid pTter44C2 which is contained in *E. coli* NRRL B-50207, wherein the polynucleotide sequence thereof encodes a polypeptide having carboxypeptidase activity. In another preferred aspect, the nucleic acid probe is the mature polypeptide coding region contained in plasmid pTter44C2 which is contained in *E. coli* NRRL B-50207.

For long probes of at least 100 nucleotides in length, very low to very high stringency conditions are defined as prehybridization and hybridization at 42° C. in 5× SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2× SSC, 0.2% SDS preferably at 45° C. (very low stringency), more preferably at 50° C. (low stringency), more preferably at 55° C. (medium stringency), more preferably at 60° C. (medium-high stringency), even more preferably at 65° C. (high stringency), and most preferably at 70° C. (very high stringency).

For short probes of about 15 nucleotides to about 70 nucleotides in length, stringency conditions are defined as prehybridization, hybridization, and washing post-hybridization at about 5° C. to about 10° C. below the calculated $T_m$, using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally.

For short probes of about 15 nucleotides to about 70 nucleotides in length, the carrier material is washed once in 6× SCC plus 0.1% SDS for 15 minutes and twice each for 15 minutes using 6× SSC at 5° C. to 10° C. below the calculated $T_m$.

In a fourth aspect, the present invention relates to artificial variants comprising a substitution, deletion, and/or insertion of one or more (or several) amino acids of the mature polypeptide of SEQ ID NO: 2, or a homologous sequence thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins, Academic Press, New York*. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in the parent polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for biological activity (i.e., carboxypeptidase activity) to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identities of essential amino acids can also be inferred from analysis of identities with polypeptides that are related to a polypeptide according to the invention.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochem.* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The total number of amino acid substitutions, deletions and/or insertions of the mature polypeptide of SEQ ID NO: 2 is 10, preferably 9, more preferably 8, more preferably 7, more preferably at most 6, more preferably 5, more preferably 4, even more preferably 3, most preferably 2, and even most preferably 1.

Sources of Polypeptides Having Carboxypeptidase Activity

A polypeptide having carboxypeptidase activity of the present invention may be obtained from microorganisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted extracellularly.

A polypeptide having carboxypeptidase activity of the present invention may be a bacterial polypeptide. For example, the polypeptide may be a gram positive bacterial polypeptide such as a *Bacillus, Streptococcus, Streptomyces, Staphylococcus, Enterococcus, Lactobacillus, Lactococcus, Clostridium, Geobacillus*, or *Oceanobacillus* polypeptide having carboxypeptidase activity, or a Gram negative bacterial polypeptide such as an *E. coli, Pseudomonas, Salmonella, Campylobacter, Helicobacter, Flavobacterium, Fusobacterium, Ilyobacter, Neisseria*, or *Ureaplasma* polypeptide having carboxypeptidase activity.

In a preferred aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* polypeptide having carboxypeptidase activity.

In another preferred aspect, the polypeptide is a *Streptococcus equisimilis, Streptococcus pyogenes, Streptococcus uberis*, or *Streptococcus equi* subsp. *Zooepidemicus* polypeptide having carboxypeptidase activity.

In another preferred aspect, the polypeptide is a *Streptomyces achromogenes, Streptomyces avermitilis, Streptomyces coelicolor, Streptomyces griseus*, or *Streptomyces lividans* polypeptide having carboxypeptidase activity.

A polypeptide having carboxypeptidase activity of the present invention may also be a fungal polypeptide, and more preferably a yeast polypeptide such as a *Candida, Kluyveromyces, Pichia, Saccharomyces, Schizosaccharomyces*, or *Yarrowia* polypeptide having carboxypeptidase activity; or more preferably a filamentous fungal polypeptide such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella*, or *Xylaria* polypeptide having carboxypeptidase activity.

In a preferred aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* polypeptide having carboxypeptidase activity.

In another preferred aspect, the polypeptide is an *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Trichoderma harzianum, Trichoderma koningii, Trichoderma longibrachiatum, Trichoderma reesei*, or *Trichoderma viride* polypeptide having carboxypeptidase activity.

In another preferred aspect, the polypeptide is a *Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila*, or *Thielavia terrestris* polypeptide In a more preferred aspect, the polypeptide is a *Thielavia terrestris* polypeptide having lipase activity. In a most preferred aspect, the polypeptide is a *Thielavia terrestris* NRRL 8126 polypeptide having lipase activity, e.g., the polypeptide comprising the mature polypeptide of SEQ ID NO: 2.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of such a microorganism. Once a polynucleotide encoding a polypeptide has been detected with the probe(s), the polynucleotide can be isolated or cloned by utilizing techniques that are well known to those of ordinary skill in the art (see, e.g., Sambrook et al., 1989, supra).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

A fusion polypeptide can further comprise a cleavage site. Upon secretion of the fusion protein, the site is cleaved releasing the polypeptide having carboxypeptidase activity from the fusion protein. Examples of cleavage sites include, but are not limited to, a Kex2 site that encodes the dipeptide Lys-Arg (Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381), an Ile-(Glu or Asp)-Gly-Arg site, which is cleaved by a Factor Xa protease after the arginine residue (Eaton et al., 1986, *Biochem.* 25: 505-512); a Asp-Asp-Asp-Asp-Lys site, which is cleaved by an enterokinase after the lysine (Collins-Racie et al., 1995, *Biotechnology* 13: 982-987); a His-Tyr-Glu site or His-Tyr-Asp site, which is cleaved by Genenase I (Carter et al., 1989, *Proteins: Structure, Function, and Genetics* 6: 240-248); a Leu-Val-Pro-Arg-Gly-Ser site, which is cleaved by thrombin after the Arg (Stevens, 2003, *Drug Discovery World* 4: 35-48); a Glu-Asn-Leu-Tyr-Phe-Gln-Gly site, which is cleaved by TEV protease after the Gln (Stevens, 2003, supra); and a Leu-Glu-Val-Leu-Phe-Gln-Gly-Pro site, which is cleaved by a genetically engineered form of human rhinovirus 3C protease after the Gln (Stevens, 2003, supra).

Polynucleotides

The present invention also relates to isolated polynucleotides comprising or consisting of nucleotide sequences that encode polypeptides having carboxypeptidase activity of the present invention.

In a preferred aspect, the nucleotide sequence comprises or consists of SEQ ID NO: 1. In another more preferred aspect, the nucleotide sequence comprises or consists of the sequence contained in plasmid pTter44C2 which is contained in *E. coli* NRRL B-50207. In another preferred aspect, the nucleotide sequence comprises or consists of the mature polypeptide coding sequence of SEQ ID NO: 1. In another preferred aspect, the nucleotide sequence comprises or consists of nucleotides 263 to 2104 of SEQ ID NO: 1. In another more preferred aspect, the nucleotide sequence comprises or consists of the mature polypeptide coding sequence contained in plasmid pTter44C2 which is contained in *E. coli* NRRL B-50207. The present invention also encompasses nucleotide sequences that encode polypeptides comprising or consisting of the amino acid sequence of SEQ ID NO: 2 or the mature polypeptide thereof, which differ from SEQ ID NO: 1 or the mature polypeptide coding sequence thereof by virtue of the degeneracy of the genetic code. The present invention also relates to subsequences of SEQ ID NO: 1 that encode fragments of SEQ ID NO: 2 having carboxypeptidase activity.

The present invention also relates to mutant polynucleotides comprising or consisting of at least one mutation in the mature polypeptide coding sequence of SEQ ID NO: 1, in which the mutant nucleotide sequence encodes the mature polypeptide of SEQ ID NO: 2.

The techniques used to isolate or clone a polynucleotide encoding a polypeptide are known in the art and include isolation from genomic DNA, preparation from cDNA, or a combination thereof. The cloning of the polynucleotides of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleotide sequence-based amplification (NASBA) may be used. The polynucleotides may be cloned from a strain of *Thielavia*, or another or related organism and thus, for example, may be an allelic or species variant of the polypeptide encoding region of the nucleotide sequence.

The present invention also relates to isolated polynucleotides comprising or consisting of nucleotide sequences having a degree of sequence identity to the mature polypeptide coding sequence of SEQ ID NO: 1 of preferably at least 80%, more preferably at least 85%, more preferably at least 90%, even more preferably at least 95%, and most preferably at least 96%, at least 97%, at least 98%, or at least 99%, which encode a polypeptide having carboxypeptidase activity.

Modification of a nucleotide sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., artificial variants that differ in specific activity, thermostability, pH optimum, or the like. The variant sequence may be constructed on the basis of the nucleotide sequence presented as the mature polypeptide coding sequence of SEQ ID NO: 1, e.g., a subsequence thereof, and/or by introduction of nucleotide substitutions that do not give rise to another amino acid sequence of the polypeptide encoded by the nucleotide sequence, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

It will be apparent to those skilled in the art that such substitutions can be made outside the regions critical to the function of the molecule and still result in an active polypeptide. Amino acid residues essential to the activity of the polypeptide encoded by an isolated polynucleotide of the invention, and therefore preferably not subject to substitution, may be identified according to procedures known in the art, such as site-directed mutagenesis or alanine-scanning mutagenesis (see, e.g., Cunningham and Wells, 1989, supra). In the latter technique, mutations are introduced at every positively charged residue in the molecule, and the resultant mutant molecules are tested for carboxypeptidase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labeling (see, e.g., de Vos et al., 1992, supra; Smith et al., 1992, supra; Wlodaver et al., 1992, supra).

The present invention also relates to isolated polynucleotides encoding polypeptides of the present invention, which hybridize under preferably very low stringency conditions, more preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 1, (ii) the genomic DNA sequence comprising the mature polypeptide coding sequence of SEQ ID NO: 1, or (iii) a full-length complementary strand of (i) or (ii); or allelic variants and subsequences thereof (Sambrook et al., 1989, supra), as defined herein.

The present invention also relates to isolated polynucleotides obtained by (a) hybridizing a population of DNA under preferably very low stringency conditions, more preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 1, (ii) the genomic DNA sequence comprising the mature polypeptide coding sequence of SEQ ID NO: 1, or (iii) a full-length complementary strand of (i) or (ii); and (b) isolating the hybridizing polynucleotide, which encodes a polypeptide having carboxypeptidase activity.

Nucleic Acid Constructs

The present invention also relates to nucleic acid constructs comprising an isolated polynucleotide of the present invention operably linked to one or more (several) control sequences that direct the expression of the coding sequence in a suitable host cell under conditions compatible with the control sequences.

An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence that is recognized by a host cell for expression of a polynucleotide encoding a polypeptide of the present invention. The promoter sequence contains transcriptional control sequences that mediate the expression of the polypeptide. The promoter may be any nucleotide sequence that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American,* 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Dania (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as a NA2-tpi promoter (a modified promoter including a gene encoding a neutral alpha-amylase in Aspergilli in which the untranslated leader has been replaced by an untranslated leader from a gene encoding triose phosphate isomerase in Aspergilli; non-limiting examples include modified promoters including the gene encoding neutral alpha-amylase in *Aspergillus niger* in which the untranslated leader has been replaced by an untranslated leader from the gene encoding triose phosphate isomerase in *Aspergillus nidulans* or *Aspergillus oryzae*); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator that is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA that is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and, when transcribed, is recognized by the host cell as a signal to add polyadenosine residues to transcribed mRNA. Any polyadenylation sequence that is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding sequence that encodes a signal peptide linked to the amino terminus of a polypeptide and directs the encoded polypeptide into the cell's secretory pathway. The 5' end of the coding sequence of the nucleotide sequence may inherently contain a signal peptide coding sequence naturally linked in translation reading frame with the segment of the coding sequence that encodes the secreted polypeptide. Alternatively, the 5' end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of a host cell of choice, i.e., secreted into a culture medium, may be used in the present invention.

Effective signal peptide coding sequences for bacterial host cells are the signal peptide coding sequences obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola insolens* endoglucanase V, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

In a preferred aspect, the signal peptide comprises or consists of amino acids 1 to 31 of SEQ ID NO: 2. In another preferred aspect, the signal peptide coding sequence comprises or consists of nucleotides 170 to 262 of SEQ ID NO: 1.

The control sequence may also be a propeptide coding sequence that encodes a propeptide positioned at the amino terminus of a polypeptide. The resultant polypeptide is known as a proenzyme or propolypeptide (or a zymogen in some cases). A propeptide is generally inactive and can be converted to a mature active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide sequences are present at the amino terminus of a polypeptide, the propeptide sequence is positioned next to the amino terminus of a polypeptide and the signal peptide sequence is positioned next to the amino terminus of the propeptide sequence.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the nucleotide sequence encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleic acids and control sequences described herein may be joined together to produce a recombinant expression vector that may include one or more (several) convenient restriction sites to allow for insertion or substitution of the nucleotide sequence encoding the polypeptide at such sites. Alternatively, a polynucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vectors of the present invention preferably contain one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers that confer antibiotic resistance such as ampicillin, kanamycin, chloramphenicol, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising an isolated polynucleotide of the present invention operably linked to one or more (several) control sequences that direct the production of a polypeptide having carboxypeptidase activity. A construct or vector comprising a polynucleotide of the present invention is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram positive bacterium or a Gram negative bacterium. Gram positive bacteria include, but not limited to, *Bacillus, Streptococcus, Streptomyces, Staphylococcus, Enterococcus, Lactobacillus, Lactococcus, Clostridium, Geobacillus,* and *Oceanobacillus*. Gram negative bacteria include, but not limited to, *E. coli, Pseudomonas, Salmonella, Campylobacter, Helicobacter, Flavobacterium, Fusobacterium, Ilyobacter, Neisseria,* and *Ureaplasma*.

The bacterial host cell may be any *Bacillus* cell. *Bacillus* cells useful in the practice of the present invention include, but are not limited to, *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, and *Bacillus thuringiensis* cells.

In a preferred aspect, the bacterial host cell is a *Bacillus amyloliquefaciens* cell. In another preferred aspect, the bacterial host cell is a *Bacillus clausii* cell. In another preferred aspect, the bacterial host cell is a *Bacillus lentus* cell. In another preferred aspect, the bacterial host cell is a *Bacillus licheniformis* cell. In another preferred aspect, the bacterial host cell is a *Bacillus stearothermophilus* cell. In another preferred aspect, the bacterial host cell is a *Bacillus subtilis* cell.

The bacterial host cell may also be any *Streptococcus* cell. *Streptococcus* cells useful in the practice of the present invention include, but are not limited to, *Streptococcus equisimilis*, *Streptococcus pyogenes*, *Streptococcus uberis*, and *Streptococcus equi* subsp. *Zooepidemicus* cells.

In a preferred aspect, the bacterial host cell is a *Streptococcus equisimilis* cell. In another preferred aspect, the bacterial host cell is a *Streptococcus pyogenes* cell. In another preferred aspect, the bacterial host cell is a *Streptococcus uberis* cell. In another preferred aspect, the bacterial host cell is a *Streptococcus equi* subsp. *Zooepidemicus* cell.

The bacterial host cell may also be any *Streptomyces* cell. *Streptomyces* cells useful in the practice of the present invention include, but are not limited to, *Streptomyces achromogenes*, *Streptomyces avermitilis*, *Streptomyces coelicolor*, *Streptomyces griseus*, and *Streptomyces lividans* cells.

In a preferred aspect, the bacterial host cell is a *Streptomyces achromogenes* cell. In another preferred aspect, the bacterial host cell is a *Streptomyces avermitilis* cell. In another preferred aspect, the bacterial host cell is a *Streptomyces coelicolor* cell. In another preferred aspect, the bacterial host cell is a *Streptomyces griseus* cell. In another preferred aspect, the bacterial host cell is a *Streptomyces lividans* cell.

The introduction of DNA into a *Bacillus* cell may, for instance, be effected by protoplast transformation (see, e.g., Chang and Cohen, 1979, *Molecular General Genetics* 168: 111-115), by using competent cells (see, e.g., Young and Spizizen, 1961, *Journal of Bacteriology* 81: 823-829, or Dubnau and Davidoff-Abelson, 1971, *Journal of Molecular Biology* 56: 209-221), by electroporation (see, e.g., Shigekawa and Dower, 1988, Biotechniques 6: 742-751), or by conjugation (see, e.g., Koehler and Thorne, 1987, *Journal of Bacteriology* 169: 5271-5278). The introduction of DNA into an *E. coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may, for instance, be effected by protoplast transformation and electroporation (see, e.g., Gong et al., 2004, *Folia Microbiol.* (Praha) 49: 399-405), by conjugation (see, e.g., Mazodier et al., 1989, *J. Bacteriol.* 171: 3583-3585), or by transduction (see, e.g., Burke et al., 2001, *Proc. Natl. Acad. Sci. USA* 98: 6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios.* 68: 189-207, by electroporation (see, e.g., Buckley et al., 1999, *Appl. Environ. Microbiol.* 65: 3800-3804) or by conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, Soc. App. Bacteriol. Symposium Series No. 9, 1980).

In an even more preferred aspect, the yeast host cell is a *Candida*, *Hansenula*, *Kluyveromyces*, *Pichia*, *Saccharomyces*, *Schizosaccharomyces*, or *Yarrowia* cell.

In a most preferred aspect, the yeast host cell is a *Saccharomyces carlsbergensis* cell. In another most preferred aspect, the yeast host cell is a *Saccharomyces cerevisiae* cell. In another most preferred aspect, the yeast host cell is a *Saccharomyces diastaticus* cell. In another most preferred aspect, the yeast host cell is a *Saccharomyces douglasii* cell. In another most preferred aspect, the yeast host cell is a *Saccharomyces kluyveri* cell. In another most preferred aspect, the yeast host cell is a *Saccharomyces norbensis* cell. In another most preferred aspect, the yeast host cell is a *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium*, *Aspergillus*, *Aureobasidium*, *Bjerkandera*, *Ceriporiopsis*, *Chrysosporium*, *Coprinus*, *Coriolus*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Phanerochaete*, *Phlebia*, *Piromyces*, *Pleurotus*, *Schizophyllum*, *Talaromyces*, *Thermoascus*, *Thielavia*, *Tolypocladium*, *Trametes*, or *Trichoderma* cell.

In a most preferred aspect, the filamentous fungal host cell is an *Aspergillus awamori*, *Aspergillus fumigatus*, *Aspergillus foetidus*, *Aspergillus japonicus*, *Aspergillus nidulans*, *Aspergillus niger* or *Aspergillus oryzae* cell. In another most preferred aspect, the filamentous fungal host cell is a *Fusarium bactridioides*, *Fusarium cerealis*, *Fusarium crook-*

*wellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum* cell. In another most preferred aspect, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

In another most preferred aspect, the filamentous fungal host cell is an *Aspergillus niger* cell. In another most preferred aspect, the filamentous fungal host cell is an *Aspergillus oryzae* cell. In another most preferred aspect, the filamentous fungal host cell is a *Chrysosporium lucknowense* cell. In another most preferred aspect, the filamentous fungal host cell is a *Fusarium venenatum* cell. In another most preferred aspect, the filamentous fungal host cell is a *Myceliophthora thermophila* cell. In another most preferred aspect, the filamentous fungal host cell is a *Trichoderma reesei* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods of producing a polypeptide of the present invention, comprising: (a) cultivating a cell, which in its wild-type form produces the polypeptide, under conditions conducive for production of the polypeptide; and (b) recovering the polypeptide. In a preferred aspect, the cell is of the genus *Thielavia*. In a more preferred aspect, the cell is *Thielavia terrestris*. In a most preferred aspect, the cell is *Thielavia terrestris* NRRL 8126.

The present invention also relates to methods of producing a polypeptide of the present invention, comprising: (a) cultivating a recombinant host cell, as described herein, under conditions conducive for production of the polypeptide; and (b) recovering the polypeptide.

The present invention also relates to methods of producing a polypeptide of the present invention, comprising: (a) cultivating a recombinant host cell under conditions conducive for production of the polypeptide, wherein the host cell comprises a mutant nucleotide sequence having at least one mutation in the mature polypeptide coding sequence of SEQ ID NO: 1, wherein the mutant nucleotide sequence encodes a polypeptide that comprises or consists of the mature polypeptide of SEQ ID NO: 2; and (b) recovering the polypeptide.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted into the medium, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure polypeptides.

Plants

The present invention also relates to plants, e.g., a transgenic plant, plant part, or plant cell, comprising an isolated polynucleotide encoding a polypeptide having carboxypeptidase activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilisation of the invention are also considered plant parts, e.g., embryos, endosperms, aleurone and seeds coats.

Also included within the scope of the present invention are the progeny of such plants, plant parts, and plant cells.

The transgenic plant or plant cell expressing a polypeptide of the present invention may be constructed in accordance with methods known in the art. In short, the plant or plant cell is constructed by incorporating one or more (several) expression constructs encoding a polypeptide of the present invention into the plant host genome or chloroplast genome and propagating the resulting modified plant or plant cell into a transgenic plant or plant cell.

The expression construct is conveniently a nucleic acid construct that comprises a polynucleotide encoding a polypeptide of the present invention operably linked with appropriate regulatory sequences required for expression of the nucleotide sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, and the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant and Cell Physiology* 39: 885-889), a *Vicia faba* promoter from the legumin B4 and the unknown seed protein gene from *Vicia faba* (Conrad et al., 1998, *Journal of Plant Physiology* 152: 708-711), a promoter from a seed oil body protein (Chen et al., 1998, *Plant and Cell Physiology* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991-1000, the *chlorella* virus adenine methyltransferase gene promoter (Mitra and Higgins, 1994, *Plant Molecular Biology* 26: 85-93), or the aldP gene promoter from rice (Kagaya et al., 1995, *Molecular and General Genetics* 248: 668-674), or a wound inducible promoter such as the potato pin2 promoter (Xu et al., 1993, *Plant Molecular Biology* 22: 573-588). Likewise, the promoter may be inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide of the present invention in the plant. For instance, the promoter enhancer element may be an intron that is placed between the promoter and the nucleotide sequence encoding a polypeptide of the present invention. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275-281; Shimamoto, 1994, *Current Opinion Biotechnology* 5: 158-162; Vasil et al., 1992, *Bio/Technology* 10: 667-674). An alternative method for transformation of monocots is based on protoplast transformation as described by Omirulleh et al., 1993, *Plant Molecular Biology* 21: 415-428. Additional transformation methods for use in accordance with the present disclosure include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well-known in the art. Often the transformation procedure is designed for the selective elimination of selection genes either during regeneration or in the following generations by using, for example, co-transformation with two separate T-DNA constructs or site specific excision of the selection gene by a specific recombinase.

The present invention also relates to methods of producing a polypeptide of the present invention comprising: (a) cultivating a transgenic plant or a plant cell comprising a polynucleotide encoding the polypeptide having carboxypeptidase activity of the present invention under conditions conducive for production of the polypeptide; and (b) recovering the polypeptide.

In embodiments, in addition to direct transformation of a particular plant genotype with a construct prepared according to the present invention, transgenic plants may be made by crossing a plant having a construct of the present invention to a second plant lacking the construct. For example, a construct encoding a polypeptide having carboxypeptidase activity or a portion thereof can be introduced into a particular plant variety by crossing, without the need for ever directly transforming a plant of that given variety. Therefore, the present invention not only encompasses a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention, or a portion of a DNA construct prepared in accordance with the present invention. In embodiments, crossing results in a transgene of the present invention being introduced into a plant line by cross pollinating a starting line with a donor plant line that includes a transgene of the present invention. Non-limiting examples of such steps are further articulated in U.S. Pat. No. 7,151,204.

It is envisioned that plants including a polypeptide having carboxypeptidase activity of the present invention include plants generated through a process of backcross conversion. For examples, plants of the present invention include plants referred to as a backcross converted genotype, line, inbred, or hybrid.

In embodiments, genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

Removal or Reduction of Carboxypeptidase Activity

The present invention also relates to methods of producing a mutant of a parent cell, which comprises disrupting or deleting a polynucleotide, or a portion thereof, encoding a polypeptide of the present invention, which results in the mutant cell producing less of the polypeptide than the parent cell when cultivated under the same conditions.

The mutant cell may be constructed by reducing or eliminating expression of a nucleotide sequence encoding a polypeptide of the present invention using methods well known in the art, for example, insertions, disruptions, replacements, or deletions. In a preferred aspect, the nucleotide sequence is inactivated. The nucleotide sequence to be modified or inactivated may be, for example, the coding region or a part thereof essential for activity, or a regulatory element required for the expression of the coding region. An example of such a regulatory or control sequence may be a promoter sequence or a functional part thereof, i.e., a part that is sufficient for affecting expression of the nucleotide sequence. Other control sequences for possible modification include, but are not limited to, a leader, polyadenylation sequence, propeptide sequence, signal peptide sequence, transcription terminator, and transcriptional activator.

Modification or inactivation of the nucleotide sequence may be performed by subjecting the parent cell to mutagenesis and selecting for mutant cells in which expression of the nucleotide sequence has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the nucleotide sequence may be accomplished by introduction, substitution, or removal of one or more (several) nucleotides in the gene or a regulatory element required for the transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the nucleotide sequence to be modified, it is preferred that the modification be performed in vitro as exemplified below.

An example of a convenient way to eliminate or reduce expression of a nucleotide sequence by a cell is based on techniques of gene replacement, gene deletion, or gene disruption. For example, in the gene disruption method, a nucleic acid sequence corresponding to the endogenous nucleotide sequence is mutagenized in vitro to produce a defective nucleic acid sequence that is then transformed into the parent cell to produce a defective gene. By homologous recombination, the defective nucleic acid sequence replaces the endogenous nucleotide sequence. It may be desirable that the defective nucleotide sequence also encodes a marker that may be used for selection of transformants in which the nucleotide sequence has been modified or destroyed. In a particularly preferred aspect, the nucleotide sequence is disrupted with a selectable marker such as those described herein.

Alternatively, modification or inactivation of the nucleotide sequence may be performed by established anti-sense or RNAi techniques using a sequence complementary to the nucleotide sequence. More specifically, expression of the nucleotide sequence by a cell may be reduced or eliminated by introducing a sequence complementary to the nucleotide sequence of the gene that may be transcribed in the cell and is capable of hybridizing to the mRNA produced in the cell. Under conditions allowing the complementary anti-sense nucleotide sequence to hybridize to the mRNA, the amount of protein translated is thus reduced or eliminated.

The present invention further relates to a mutant cell of a parent cell that comprises a disruption or deletion of a nucleotide sequence encoding the polypeptide or a control sequence thereof, which results in the mutant cell producing less of the polypeptide or no polypeptide compared to the parent cell.

The polypeptide-deficient mutant cells so created are particularly useful as host cells for the expression of native and/or heterologous polypeptides. Therefore, the present invention further relates to methods of producing a native or heterologous polypeptide, comprising: (a) cultivating the mutant cell under conditions conducive for production of the polypeptide; and (b) recovering the polypeptide. The term "heterologous polypeptides" is defined herein as polypeptides that are not native to the host cell, a native protein in which modifications have been made to alter the native sequence, or a native protein whose expression is quantitatively altered as a result of a manipulation of the host cell by recombinant DNA techniques.

In a further aspect, the present invention relates to a method of producing a protein product essentially free of carboxypeptidase activity by fermentation of a cell that produces both a polypeptide of the present invention as well as the protein product of interest by adding an effective amount of an agent capable of inhibiting carboxypeptidase activity to the fermentation broth before, during, or after the fermentation has been completed, recovering the product of interest from the fermentation broth, and optionally subjecting the recovered product to further purification.

In a further aspect, the present invention relates to a method of producing a protein product essentially free of carboxypeptidase activity by cultivating the cell under conditions permitting the expression of the product, subjecting the resultant culture broth to a combined pH and temperature treatment so as to reduce the carboxypeptidase activity substantially, and recovering the product from the culture broth. Alternatively, the combined pH and temperature treatment may be performed on an enzyme preparation recovered from the culture broth. The combined pH and temperature treatment may optionally be used in combination with a treatment with a carboxypeptidase inhibitor.

In accordance with this aspect of the invention, it is possible to remove at least 60%, preferably at least 75%, more preferably at least 85%, still more preferably at least 95%, and most preferably at least 99% of the carboxypeptidase activity. Complete removal of carboxypeptidase activity may be obtained by use of this method.

The combined pH and temperature treatment is preferably carried out at a pH in the range of 2-4 or 9-11 and a temperature in the range of at least 60-70° C. for a sufficient period of time to attain the desired effect, where typically, 30 to 60 minutes is sufficient.

The methods used for cultivation and purification of the product of interest may be performed by methods known in the art.

The methods of the present invention for producing an essentially carboxypeptidase-free product is of particular interest in the production of eukaryotic polypeptides, in particular fungal proteins such as enzymes. The enzyme may be selected from, e.g., an amylolytic enzyme, lipolytic enzyme, proteolytic enzyme, cellulolytic enzyme, oxidoreductase, or plant cell-wall degrading enzyme. Examples of such enzymes include an aminopeptidase, amylase, amyloglucosidase, carbohydrase, carboxypeptidase, catalase, cellobiohydrolase, cellulase, chitinase, cutinase, cyclodextrin glycosyltransferase, deoxyribonuclease, endoglucanase, esterase, galactosidase, beta-galactosidase, glucoamylase, glucose oxidase, glucosidase, haloperoxidase, hemicellulase, invertase, isomerase, laccase, ligase, lipase, lyase, mannosidase, oxidase, pectinolytic enzyme, peroxidase, phytase, phenoloxidase, polyphenoloxidase, proteolytic enzyme, ribonuclease, transferase, transglutaminase, or xylanase. The carboxypeptidase-deficient cells may also be used to express heterologous proteins of pharmaceutical interest such as hormones, growth factors, receptors, and the like.

It will be understood that the term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from carboxypeptidase activity that is produced by a method of the present invention.

Methods of Inhibiting Expression of a Polypeptide Having Carboxypeptidase Activity The present invention also relates to methods of inhibiting the expression of a polypeptide having carboxypeptidase activity in a cell, comprising administering to the cell or expressing in the cell a double-stranded RNA (dsRNA) molecule, wherein the dsRNA comprises a subsequence of a polynucleotide of the present invention. In a preferred aspect, the dsRNA is about 15, 16, 17, 18, 19, 20, 21, 22, 23, 24, 25 or more duplex nucleotides in length.

The dsRNA is preferably a small interfering RNA (siRNA) or a micro RNA (miRNA). In a preferred aspect, the dsRNA is small interfering RNA (siRNAs) for inhibiting transcription. In another preferred aspect, the dsRNA is micro RNA (miRNAs) for inhibiting translation.

The present invention also relates to such double-stranded RNA (dsRNA) molecules, comprising a portion of the mature polypeptide coding sequence of SEQ ID NO: 1 for inhibiting expression of a polypeptide having carboxypeptidase activity in a cell. While the present invention is not limited by any particular mechanism of action, the dsRNA can enter a cell and cause the degradation of a single-stranded RNA (ssRNA) of similar or identical sequences, including endogenous mRNAs. When a cell is exposed to dsRNA, mRNA from the homologous gene is selectively degraded by a process called RNA interference (RNAi).

The dsRNAs of the present invention can be used in gene-silencing. In one aspect, the invention provides methods to selectively degrade RNA using the dsRNAis of the present invention. The process may be practiced in vitro, ex vivo or in vivo. In one aspect, the dsRNA molecules can be used to generate a loss-of-function mutation in a cell, an organ or an animal. Methods for making and using dsRNA molecules to selectively degrade RNA are well known in the art, see, for example, U.S. Pat. Nos. 6,506,559; 6,511,824; 6,515,109; and 6,489,127.

Compositions

The present invention also relates to compositions comprising a polypeptide of the present invention. Preferably, the compositions are enriched in such a polypeptide. The term "enriched" indicates that the carboxypeptidase activity of the composition has been increased, e.g., with an enrichment factor of at least 1.1.

The composition may comprise a polypeptide of the present invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by a microorganism belonging to the genus *Aspergillus*, preferably *Aspergillus aculeatus*, *Aspergillus awamori*, *Aspergillus fumigatus*, *Aspergillus foetidus*, *Aspergillus japonicus*, *Aspergillus nidulans*, *Aspergillus niger*, or *Aspergillus oryzae*; *Fusarium*, preferably *Fusarium bactridioides*,

*Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sulphureum, Fusarium toruloseum, Fusarium trichothecioides,* or *Fusarium venenatum; Humicola,* preferably *Humicola insolens* or *Humicola lanuginosa*; or *Trichoderma,* preferably *Trichoderma harzianum, Trichoderma koningii, Trichoderma longibrachiatum, Trichoderma reesei,* or *Trichoderma viride.*

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

In a preferred aspect, the invention relates to a flavor-improving composition comprising a polypeptide with carboxypeptidase activity. In another preferred aspect, the flavor-improving composition further comprises an endopeptidase. In another preferred aspect, the flavoring composition further comprises one or more unspecific-acting endo- and/or exo-peptidase enzymes. In another preferred aspect, the flavoring composition further comprises one or more specific-acting endo- and/or exo-peptidase enzymes.

In a preferred aspect, the specific acting proteolytic enzyme is an endopeptidase such as a glutamyl endopeptidase (EC 3.4.21.19); a lysyl endopeptidase (EC 3.4.21.50); a leucyl endopeptidase (EC 3.4.21.57); a glycyl endopeptidase (EC 3.4.22.25); a prolyl endopeptidase (EC 3.4.21.26); trypsin (EC 3.4.21.4) or a trypsin-like (lysine/arginine specific) endopeptidase; or a peptidyl-Asp metalloendopeptidase (EC 3.4.24.33).

The glutamyl endopeptidase (EC 3.4.21.19) may preferably be obtained from a strain of *Bacillus,* in particular *Bacillus licheniformis* and *Bacillus subtilis,* a strain of *Staphylococcus,* in particular *Staphylococcus aureus,* a strain of *Streptomyces,* in particular *Streptomyces thermovulgaris* and *Streptomyces griseus,* or a strain of *Actinomyces* sp.

The lysyl endopeptidase (EC 3.4.21.50) may preferably be obtained from a strain of *Achromobacter,* in particular *Achromobacter lyticus,* a strain of *Lysobacter,* in particular *Lysobacter enzymogenes,* or a strain of *Pseudomonas,* in particular *Pseudomonas aeruginosa.*

The leucyl endopeptidase (EC 3.4.21.57) may be of plant origin.

The glycyl endopeptidase (EC 3.4.22.25) may preferably be obtained from the papaya plant (*Carica papaya*).

The prolyl endopeptidase (EC 3.4.21.26) may preferably be obtained from a strain of *Flavobacterium,* or it may be of plant origin.

The trypsin-like endopeptidase may preferably be obtained from a strain of *Fusarium,* in particular *Fusarium oxysporum,* e.g., as described in WO 89/06270 or WO 94/25583.

The peptidyl-Asp metalloendopeptidase (EC 3.4.24.33) may preferably be obtained from a strain of *Pseudomonas,* in particular *Pseudomonas fragi.*

In another preferred aspect, the specific acting proteolytic enzyme is an exo-peptidase that may act from either end of the peptide.

In a preferred aspect, the specific acting proteolytic enzyme is an aminopeptidase such as a leucyl aminopeptidase (EC 3.4.11.1); or a tripeptide aminopeptidase (EC 3.4.11.4).

In another preferred aspect, the specific acting proteolytic enzyme is a carboxypeptidase such as a proline carboxypeptidase (EC 3.4.16.2); a carboxypeptidase A (EC 3.4.17.1); a carboxypeptidase B (EC 3.4.17.2); a carboxypeptidase C (EC 3.4.16.5); a carboxypeptidase D (EC 3.4.16.6); a lysine (arginine) carboxypeptidase (EC 3.4.17.3); a glycine carboxypeptidase (EC 3.4.17.4); an alanine carboxypeptidase (EC 3.4.17.6); a glutamate carboxypeptidase (EC 3.4.17.11); a peptidyl-dipeptidase A (EC 3.4.15.1); or a peptidyl-dipeptidase (EC 3.4.15.5).

The polypeptide compositions may be prepared in accordance with methods known in the art and may be in the form of a liquid or a dry composition. The polypeptide may be stabilized by methods known in the art.

The present invention also relates to food products, e.g., baked products, comprising a protein hydrolysate obtained by the methods of the present invention. Such food products exhibit enhanced organoleptic qualities, such as improvement in flavor, palatability, mouth feel, aroma, and crust color.

In the present context, the term Abaked products@ includes any food prepared from dough, either of a soft or a crisp character. Examples of baked products, whether of a white, light or dark type, which may be advantageously produced by the present invention, are bread, in particular white, whole-meal or rye bread, typically in the form of loaves or rolls; French baguette-type breads; pita breads; tacos; cakes; pancakes; biscuits; crisp breads; and the like.

Such baked products are conventionally prepared from a dough which comprises flour and water, and which is typically leavened. The dough may be leavened in various ways, such as by adding sodium bicarbonate or the like, or by adding a leaven (fermenting dough), but the dough is preferably leavened by adding a suitable yeast culture such as a culture of *Saccharomyces cerevisiae* (baker's yeast). Any of the commercially available *Saccharomyces cerevisiae* strains may be employed.

Further, the dough used in the preparation of the baked products may be fresh or frozen. The preparation of frozen dough is described by K. Kulp and K. Lorenz in "Frozen and Refrigerated Doughs and Batters". A flavor improving composition of the present invention is typically included in the dough in an amount in the range of 0.01-5%, more preferably 0.1-3%.

In the methods of the present invention, a polypeptide of the present invention, an endopeptidase, a transglutaminase, a peptidoglutaminase, one or more specific and/or unspecific acting endo- and/or exo-peptidase enzymes, and/or one or more enzymes specified above may be added, either separately or concurrently, to the mixture from which the dough is made or to any ingredient, e.g., flour, from which the dough is to be made.

The present invention further relates to a pre-mix, e.g., in the form of a flour composition, for dough and/or baked products made from dough, wherein the pre-mix comprises a flavor-improving composition of the invention and optionally one or more other enzymes specified above.

In another aspect, the pre-mix comprises a hydrolysate obtained by the methods of the invention.

The pre-mix may be prepared by mixing the relevant enzymes with a suitable carrier such as flour, starch, a sugar or a salt. The pre-mix may contain other dough-improving and/or bread-improving additives.

In the present invention, the term "pre-mix" is a mixture of baking agents, normally including flour, which has been prepared to permit storage under designated conditions and provide convenience in handling during dough preparation processes. Such a pre-mix may be of advantageous use in industrial and commercial bread-baking plants and facilities, as well as in retail bakeries.

The present invention also relates to the use of a hydrolysate produced by the methods of the present invention described herein as an additive to food products, such as baked foods, to enhance organoleptic qualities, such as flavor, palatability and aroma.

The hydrolysates enriched in free glutamic acid and/or peptide bound glutamic acid residues obtained by the methods of the present invention may be used in various industrial applications, in particular, where there is a need for the incorporation of functional proteins.

For example, the present invention also relates to food products comprising a hydrolysate enriched in free glutamic acid and/or peptide bound glutamic acid residues obtained by the method of the invention and to animal feed additives comprising a hydrolysate enriched in free glutamic acid and/or peptide bound glutamic acid residues obtained by the methods of the present invention.

Other examples are given below of preferred uses of the polypeptide compositions of the invention. The dosage of the polypeptide composition of the invention and other conditions under which the composition is used may be determined on the basis of methods known in the art.

Uses

The present invention is also directed to methods for using the polypeptides having carboxypeptidase activity, or compositions thereof.

The polypeptides of the present invention may be used in the production of protein hydrolysates for enhancing the degree of hydrolysis and flavor development.

The present invention further relates to methods for the use of a polypeptide of the present invention in combination with an endopeptidase to produce a high degree of hydrolysis of a protein-rich material. The method comprises treatment of a proteinaceous substrate with the polypeptide and an endopeptidase. The substrate may be treated with the enzymes concurrently or consecutively.

A polypeptide of the present invention is added to the proteinaceous substrate in an effective amount conventionally employed in protein hydrolysis processes, preferably in the range of from about 0.1 to about 100,000 CPDU per 100 g of protein, and more preferably in the range of from about 1 to about 10,000 CPDU per 100 g of protein. As defined herein, one CPDU (carboxypeptidase unit) is the amount of carboxypeptidase which liberates 1 micromole of glutamate per minute from a 0.5 mM N-CBZ-Ala-Glu (Sigma Chemical Co., St. Louis Mo.) solution at pH 4.5 and 25EC.

The endopeptidase may be obtained from a strain of *Bacillus*, preferably *Bacillus licheniformis* or *Bacillus subtilis*, a strain of *Staphylococcus*, preferably *Staphylococcus aureus*, a strain of *Streptomyces*, preferably *Streptomyces thermovularis* or *Streptomyces griseus*, a strain of *Actinomyces* species, a strain of *Aspergillus*, preferably *Aspergillus aculeatus, Aspergillus awamori, Aspergillus foetidus, Aspergillus nidulans, Aspergillus niger*, or *Aspergillus oryzae*, or a strain of *Fusarium*, preferably *Fusarium venenatum*.

The endopeptidase is added to the proteinaceous substrate in an effective amount conventionally employed in protein hydrolysis processes, preferably in the range of from about 0.05 to about 15 AU/100 g of protein, and more preferably from about 0.1 to about 8 AU/100 g of protein. One AU (Anson Unit) is defined as the amount of enzyme which under standard conditions (i.e., 25EC, pH 7.5 and 10 minutes reaction time) digests hemoglobin at an initial rate such that there is liberated per minute an amount of TCA soluble product which gives the same color with phenol reagent as one milliequivalent of tyrosine. The analytical method AF 4/5 is available upon request from Novozymes A/S, Denmark, which is incorporated herein by reference.

The enzymatic treatment, i.e., the incubation of the substrate with the enzyme preparations, may take place at any convenient temperature at which the enzyme preparation does not become inactivated, preferably in the range of from about 20EC to about 70EC. In accordance with established practice, the enzyme preparations may be suitably inactivated by increasing the temperature of the incubation mixture to a temperature where the enzymes become inactivated, e.g., to above about 70EC, or similarly by decreasing the pH of the incubation mixture to a point where the enzymes become inactivated, e.g., below about 4.0.

Furthermore, the methods of the present invention result in enhancement of the degree of hydrolysis of a proteinaceous substrate. As used herein, the degree of hydrolysis (DH) is the percentage of the total number of amino bonds in a protein that has been hydrolyzed by a proteolytic enzyme.

The present invention also relates to methods of obtaining a hydrolysate enriched in free glutamic acid and/or peptide bound glutamic acid residues, which method comprises:

(a) subjecting the substrate to a deamidation process; and
(b) subjecting the substrate to the action of a polypeptide having carboxypeptidase activity.

The two steps may be performed simultaneously, or the second step may be performed subsequent to the first step.

These methods of the present invention produce protein hydrolysates of excellent flavor because glutamic acid (Glu), whether free or peptide bound, plays an important role in the flavor and palatability of protein hydrolysates. These method also produce protein hydrolysates having improved functionality, in particular, improved solubility, improved emulsifying properties, increased degree of hydrolysis, and improved foaming properties.

The conversion of amides (glutamine or asparagine) into charged acids (glutamic acid or aspartic acid) via the liberation of ammonia is known as deamidation. Deamidation may take place as a non-enzymatic or as an enzymatic deamidation process.

In a preferred aspect, the deamidation is carried out as an enzymatic deamidation process, e.g., by subjecting the substrate to a transglutaminase and/or peptidoglutaminase.

The transglutaminase may be obtained from any convenient source including mammals, see e.g., JP 1050382 and JP 5023182, including activated Factor XIII, see e.g., WO 93/15234; those derived from fish, see e.g., EP 555,649; and those obtained from microorganisms, see e.g., EP 379,606, WO 96/06931 and WO 96/22366. In a preferred aspect, the transglutaminase is obtained from an Oomycete, including a strain of *Phytophthora*, preferably *Phytophthora cactorum*, or a strain of *Pythium*, preferably *Pythium irregulare, Pythium* sp., *Pythium intermedium, Pythium ultimum*, or *Pythium periilum* (or *Pythium periplocum*). In another preferred aspect, the transglutaminase is of bacterial origin and is obtained from a strain of *Bacillus*, preferably *Bacillus subtilis*, a strain of *Streptoverticillium*, preferably *Streptoverticillium mobaraensis, Streptoverticillium griseocarneum*, or *Streptoverticillium cinnamoneum*, and a strain of *Streptomyces*, preferably *Streptomyces lydicus*.

The peptidoglutaminase may be a peptidoglutaminase I (peptidyl-glutaminase; EC 3.5.1.43), or a peptidoglutaminase II (protein-glutamine glutaminase; EC 3.5.1.44), or any mixture thereof. The peptidoglutaminase may be obtained from a strain of *Aspergillus*, preferably *Aspergillus japonicus*, a strain of *Bacillus*, preferably *Bacillus circulans*, a strain of *Cryptococcus*, preferably *Cryptococcus albidus*, or a strain of *Debaryomyces*, preferably *Debaryomyces kloecheri*.

The transglutaminase is added to the proteinaceous substrate in an effective amount conventionally employed in deamidation processes, preferably in the range of from about 0.01 to about 5% (w/w), and more preferably in the range of from about 0.1 to about 1% (w/w) of enzyme preparation relating to the amount of substrate.

The peptidoglutaminase is added to the proteinaceous substrate in an effective amount conventionally employed in deamidation processes, preferably in the range of from about 0.01 to about 100,000 PGase Units per 100 g of substrate, and more preferably in the range of from about 0.1 to about 10,000 PGase Units per 100 g of substrate.

The peptidoglutaminase activity may be determined according to the procedure of Cedrangoro et al. (1965, *Enzymologia* 29: 143). According to this procedure, 0.5 ml of an enzyme sample, adjusted to pH 6.5 with 1 N NaOH, is charged into a small vessel. Then 1 ml of a borate pH 10.8 buffer solution is added to the vessel. The discharged ammonia is absorbed by 5 N sulphuric acid, and by use of Nessler=s reagent the mixture is allowed to form color which is measured at 420 nm. One PGase unit is the amount of enzyme capable of producing 1 micromole of ammonia per minute under these conditions.

Alternatively, the peptidoglutaminase activity may be determined according to the procedure described in U.S. Pat. No. 3,857,967.

In step (b) of the methods of the present invention, the substrate is subjected to a polypeptide of the present invention. A polypeptide of the present invention is added to the proteinaceous substrate in an effective amount conventionally employed in protein hydrolysis processes, preferably in the range of from about 0.001 to about 0.5 AU/100 g of substrate, more preferably in the range of from about 0.01 to about 0.1 AU/100 g of substrate.

In another aspect, the methods of the present invention for producing a hydrolysate enriched in free glutamic acid and/or peptide bound glutamic acid residues further comprise:

(c) subjecting the substrate to one or more unspecific acting endo- and/or exo-peptidase enzymes.

This step may take place simultaneously with steps (a) and (b), or may follow steps (a) and (b).

In a preferred aspect, the unspecific acting endo- and/or exo-peptidase enzyme is obtained from a strain of *Aspergillus*, preferably *Aspergillus niger*, *Aspergillus oryzae*, or *Aspergillus sojae*, or a strain of *Bacillus*, preferably *Bacillus amyloliquefaciens*, *Bacillus lentus*, *Bacillus licheniformis*, or *Bacillus subtilis*.

The unspecific acting endo- and/or exo-peptidase enzyme is added to the substrate in an effective amount conventionally employed in protein hydrolysis processes, preferably in the range of from about 0.05 to about 15 CPU/100 g of substrate, and more preferably in the range of from about 0.1 to about 5 CPU/100 g of substrate. One CPU (Casein Protease Unit) is defined as the amount of enzyme liberating 1 micromole of primary amino groups (determined by comparison with a serine standard) per minute from casein under standard conditions, i.e., incubation for 30 minutes at 25EC and pH 9.5. The analytical method AF 228/1, which is incorporated herein by reference, is available upon request from Novozymes A/S, Bagsværd, Denmark.

Each enzymatic treatment may take place at any temperature at which the enzyme preparation does not become inactivated, preferably in the range of from about 20EC to about 70EC. The enzyme preparation may then be inactivated by increasing the temperature, e.g., to above about 70EC, or by decreasing the pH, e.g., below about 4.0.

The proteinaceous substrate used in the methods of the present invention may consist of intact proteins, prehydrolyzed proteins (i.e., peptides), or a mixture thereof. The proteinaceous substrate may be of vegetable or animal origin. Preferably, the proteinaceous substrate is of vegetable origin, e.g., soy protein, grain protein, e.g., wheat gluten, corn gluten, barley, rye, oat, rice, zein, lupine, cotton seed protein, rape seed protein, peanut, alfalfa protein, pea protein, fabaceous bean protein, sesame seed protein, or sunflower. A proteinaceous substrate of animal origin may be whey protein, casein, meat proteins, fish protein, red blood cells, egg white, gelatin, or lactoalbumin.

The present invention also relates to protein hydrolysates produced by these methods.

A polypeptide of the present invention may also be useful for a number of purposes in which a specific cleavage of peptide sequences is desirable. For instance, some proteins or peptides are synthesized in the form of inactive precursors comprising a number of additional amino acid residues at the N-terminal of the mature protein. A polypeptide of the present invention could provide the necessary post-translational processing to activate such precursor proteins.

Signal Peptide

The present invention also relates to an isolated polynucleotide encoding a signal peptide comprising or consisting of amino acids 1 to 31 of SEQ ID NO: 2.

The present invention also relates to nucleic acid constructs comprising a gene encoding a protein, wherein the gene is operably linked to the isolated polynucleotide encoding the signal peptide, wherein the gene is foreign to the polynucleotide encoding the signal peptide.

In a preferred aspect, the isolated polynucleotide encoding a signal peptide comprises or consists of nucleotides 170 to 262 of SEQ ID NO: 1.

The present invention also relates to recombinant expression vectors and recombinant host cells comprising such nucleic acid constructs.

The present invention also relates to methods of producing a protein, comprising: (a) cultivating a recombinant host cell comprising a gene encoding a protein operably linked to such a polynucleotide encoding a signal peptide, wherein the gene is foreign to the polynucleotide encoding the signal peptide, under conditions conducive for production of the protein; and (b) recovering the protein The protein may be native or heterologous to a host cell. The term "protein" is not meant herein to refer to a specific length of the encoded product and, therefore, encompasses peptides, oligopeptides, and proteins. The term "protein" also encompasses two or more polypeptides combined to form the encoded product. The proteins also include hybrid polypeptides that comprise a combination of partial or complete polypeptide sequences obtained from at least two different proteins wherein one or more (several) may be heterologous or native to the host cell. Proteins further include naturally occurring allelic and engineered variations of the above mentioned proteins and hybrid proteins.

Preferably, the protein is a hormone or variant thereof, enzyme, receptor or portion thereof, antibody or portion thereof, or reporter. In a more preferred aspect, the protein is an oxidoreductase, transferase, hydrolase, lyase, isomerase, or ligase. In an even more preferred aspect, the protein is an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, another lipase, mannosidase, mutanase, oxidase, pectinolytic enzyme, peroxidase, phytase, polyphenoloxidase, proteolytic enzyme, ribonuclease, transglutaminase or xylanase.

The gene may be obtained from any prokaryotic, eukaryotic, or other source.

The present invention is further described by the following examples that should not be construed as limiting the scope of the invention.

EXAMPLES

Materials

Chemicals used as buffers and substrates were commercial products of at least reagent grade.

Strains

*Thielavia terrestris* NRRL 8126 was used as the source of a gene encoding a polypeptide with identity to a serine carboxypeptidase.

Media

NNCYPmod medium was composed of 1.0 g of NaCl, 5.0 g of $NH_4NO_3$, 0.2 g of $MgSO_4.7H_2O$, 0.2 g of $CaCl_2$, 2.0 g of citric acid, 1.0 g of Bacto Peptone, 5.0 g of yeast extract, 1 ml of COVE trace metals solution, sufficient $K_2HPO_4$ to achieve the final pH of approximately 5.4, and deionized water to 1 liter.

COVE trace metals solution was composed of 0.04 g of $Na_2B_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_2.2H_2O$, 10 g of $ZnSO_4.7H_2O$, and deionized water to 1 liter.

LB plates were composed of 10 g of tryptone, 5 g of yeast extract, 5 g of sodium chloride, 15 g of Bacto Agar, and deionized water to 1 liter.

LB medium was composed of 10 g of tryptone, 5 g of yeast extract, 5 g of sodium chloride, and deionized water to 1 liter.

SOC medium was composed of 2% tryptone, 0.5% yeast extract, 10 mM NaCl, 2.5 mM KCl, 10 mM $MgCl_2$, and 10 mM $MgSO_4$, sterilized by autoclaving and then filter-sterilized glucose was added to 20 mM.

Freezing medium was composed of 60% SOC and 40% glycerol.

Example 1

Expressed Sequence Tags (EST) cDNA Library Construction

*Thielavia terrestris* NRRL 8126 was cultivated in 50 ml of NNCYPmod medium supplemented with 1% glucose in a 250 ml flask at 45° C. for 24 hours with shaking at 200 rpm. A two ml aliquot from the 24-hour liquid culture was used to seed a 500 ml flask containing 100 ml of NNCYPmod medium supplemented with 2% SIGMACELL® 20 (cellulose; Sigma Chemical Co., Inc., St. Louis, Mo., USA). The culture was incubated at 45° C. for 3 days with shaking at 200 rpm. The mycelia were harvested by filtration through a funnel with a glass fiber prefilter (Nalgene, Rochester, N.Y., USA), washed twice with 10 mM Tris-HCl-1 mM EDTA pH 8 (TE), and quick frozen in liquid nitrogen.

Total RNA was isolated using the following method. Frozen mycelia of *Thielavia terrestris* NRRL 8126 were ground in an electric coffee grinder. The ground material was mixed 1:1 v/v with 20 ml of FENAZOL™ (Ambion, Inc., Austin, Tex., USA) in a 50 ml tube. Once the mycelia were suspended, they were extracted with chloroform and three times with a mixture of phenol-chloroform-isoamyl alcohol 25:24:1 v/v/v. From the resulting aqueous phase, the RNA was precipitated by adding 1/10 volume of 3 M sodium acetate pH 5.2 and 1.25 volumes of isopropanol. The precipitated RNA was recovered by centrifugation at 12,000×g for 30 minutes at 4° C. The final pellet was washed with cold 70% ethanol, air dried, and resuspended in 500 ml of diethylpyrocarbonate treated water (DEPC-water).

The quality and quantity of the purified RNA was assessed with an AGILENT® 2100 Bioanalyzer (Agilent Technologies, Inc., Palo Alto, Calif., USA). Polyadenylated mRNA was isolated from 360 µg of total RNA with the aid of a POLY(A)PURIST™ Magnetic Kit (Ambion, Inc., Austin, Tex., USA) according to the manufacturer's instructions.

To create a cDNA library, a CLONEMINER™ Kit (Invitrogen Corp., Carlsbad, Calif., USA) was employed to construct a directional library that does not require the use of restriction enzyme cloning, thereby reducing the number of chimeric clones and size bias.

To insure the successful synthesis of the cDNA, two reactions were performed in parallel with two different concentrations of mRNA (2.2 and 4.4 µg of poly $(A)^+$ mRNA). The mRNA samples were mixed with a Biotin-attB2-Oligo(dt) primer (Invitrogen Corp., Carlsbad, Calif., USA), 1× first strand buffer (Invitrogen Corp., Carlsbad, Calif., USA), 2 µl of 0.1 M dithiothreitol (DTT), 10 mM of each dNTP, and water to a final volume of 18 and 16 µl, respectively.

The reaction mixtures were mixed and then 2 and 4 µl of SUPERSCRIPT™ reverse transcriptase (Invitrogen Corp., Carlsbad, Calif., USA), respectively, were added. The reaction mixtures were incubated at 45° C. for 60 minutes to synthesize the first complementary strand. For second strand synthesis, to each first strand reaction was added 30 µl of 5× second strand buffer (Invitrogen Corp., Carlsbad, Calif., USA), 3 µl of 10 mM of each dNTP, 10 units of *E. coli* DNA ligase (Invitrogen Corp., Carlsbad, Calif., USA), 40 units of *E. coli* DNA polymerase I (Invitrogen Corp., Carlsbad, Calif., USA), and 2 units of *E. coli* RNase H (Invitrogen Corp., Carlsbad, Calif., USA) in a total volume of 150 µl. The mixtures were then incubated at 16° C. for two hours. After the two-hour incubation 2 µl of T4 DNA polymerase (Invitrogen Corp., Carlsbad, Calif., USA) were added to each reaction and incubated at 16° C. for 5 minutes to create a bunt-ended cDNA. The cDNA reactions were extracted with a mixture of phenol-chloroform-isoamyl alcohol 25:24:1 v/v/v and precipitated in the presence of 20 µg of glycogen, 120 µl of 5 M ammonium acetate, and 660 µl of ethanol. After centrifugation at 12,000×g for 30 minutes at 4° C., the cDNA pellets were washed with cold 70% ethanol, dried under vacuum for 2-3 minutes, and resuspended in 18 µl of DEPC-water. To each resuspended cDNA sample were added 10 µl of 5× adapted buffer (Invitrogen, Carlsbad, Calif.), 10 µg of each attB1 adapter (Invitrogen, Carlsbad, Calif., USA), 7 µl of 0.1 M DTT, and 5 units of T4 DNA ligase (Invitrogen, Carlsbad, Calif., USA).

Ligation reactions were incubated overnight at 16° C. Excess adapters were removed by size-exclusion chromatography in 1 ml of SEPHACRYL™ S-500 HR resin (Amersham Biosciences, Piscataway, N.J., USA). Column fractions were collected according to the CLONEMINER™ Kit's instructions and fractions 3 to 14 were analyzed with an AGILENT® 2100 Bioanalyzer to determine the fraction at which the attB1 adapters started to elute. This analysis showed that the adapters started eluting around fraction 10 or 11. For the first library fractions 6 to 11 were pooled and for the second library fractions 4-11 were pooled.

Cloning of the cDNA was performed by homologous DNA recombination according to the GATEWAY® System protocol (Invitrogen Corp., Carlsbad, Calif., USA) using BP CLO-NASE™ (Invitrogen Corp., Carlsbad, Calif., USA) as the recombinase. Each BP CLONASE™ recombination reaction contained approximately 70 ng of attB-flanked-cDNA, 250 ng of pDONR™222, 2 µl of 5× BP CLONASE™ buffer, 2 µl of TE, and 3 µl of BP CLONASE™. All reagents were obtained from Invitrogen, Carlsbad, Calif., USA. Recombination reactions were incubated at 25° C. overnight.

Heat-inactivated BP recombination reactions were then divided into 6 aliquots and electroporated into ELECTROMAX™ DH10B electrocompetent cells (Invitrogen Corp., Carlsbad, Calif., USA) using a GENE PULSER™ (Bio-Rad, Hercules, Calif., USA) with the following parameters: Voltage: 2.0 kV; Resistance: 200 Ω; and Capacity: 25 µF. Electroporated cells were resuspended in 1 ml of SOC medium and incubated at 37° C. for 60 minutes with constant shaking at 200 rpm. After the incubation period, the transformed cells were pooled and mixed 1:1 with freezing medium. A 200 µl aliquot was removed from each library for library titration and then the rest of each library was aliquoted into 1.8 ml cryovials (Wheaton Science Products, Millville, N.J., USA) and stored frozen at −80° C.

Four serial dilutions of each library were prepared: 1/100, 1/1000, 1/10$^4$, and 1/10$^5$. From each dilution, 100 µl were plated onto 150 mm LB plates supplemented with 50 µg of kanamycin per ml and incubated at 3° C. overnight. The number of colonies on each dilution plate was counted and used to calculate the total number of transformants in each library.

The first library contained approximately 5.4 million independent clones and the second library contained approximately 9 million independent clones.

Example 2

Template Preparation and Nucleotide Sequencing of cDNA Clones

Aliquots from both libraries described in Example 1 were mixed and plated onto 25×25 cm LB plates supplemented with 50 µg of kanamycin per ml. Individual colonies were arrayed onto 96-well plates containing 100 µl of LB medium supplemented with 50 µg of kanamycin per ml with the aid of a QPix Robot (Genetix Inc., Boston, Mass., USA). Forty-five 96-well plates were obtained for a total of 4320 individual clones. The plates were incubated overnight at 37° C. with shaking at 200 rpm. After incubation, 100 µl of sterile 50% glycerol was added to each well. The transformants were replicated with the aid of a 96-pin tool (Boekel, Feasterville, Pa., USA) into secondary, deep-dish 96-well microculture plates (Advanced Genetic Technologies Corporation, Gaithersburg, Md., USA) containing 1 ml of MAGNIFICENT BROTH™ (MacConnell Research, San Diego, Calif., USA) supplemented with 50 µg of kanamycin per ml in each well. The primary microtiter plates were stored frozen at −80° C. The secondary deep-dish plates were incubated at 37° C. overnight with vigorous agitation at 300 rpm on a rotary shaker. To prevent spilling and cross-contamination, and to allow sufficient aeration, each secondary culture plate was covered with a polypropylene pad (Advanced Genetic Technologies Corporation, Gaithersburg, Md., USA) and a plastic microtiter dish cover. Plasmid DNA was prepared with a Robot-Smart 384 (MWG Biotech Inc., High Point, N.C., USA) and a MONTAGE™ Plasmid Miniprep Kit (Millipore, Billerica, Mass., USA).

Sequencing reactions were performed using BIGDYE® (Applied Biosystems, Inc., Foster City, Calif., USA) terminator chemistry (Giesecke et al., 1992, *Journal of Virology Methods* 38: 47-60) and a M13 Forward (−20) sequencing primer:

(SEQ ID NO: 3)
5'-GTAAAACGACGGCCAG-3'

The sequencing reactions were performed in a 384-well format with a Robot-Smart 384. Terminator removal was performed with a MULTISCREEN® Seq384 Sequencing Clean-up Kit (Millipore, Billerica, Mass., USA). Reactions contained 6 µl of plasmid DNA and 4 µl of sequencing mastermix (Applied Biosystems, Foster City, Calif., USA) containing 1 µl of 5× sequencing buffer (Millipore, Billerica, Mass., USA), 1 µl of BIGDYE® terminator (Applied Biosystems, Inc., Foster City, Calif., USA), 1.6 pmoles of M13 Forward primer, and 1 µl of water. Single-pass DNA sequencing was performed with an ABI PRISM Automated DNA Sequencer Model 3700 (Applied Biosystems, Foster City, Calif., USA).

Example 3

Analysis of DNA Sequence Data of cDNA Clones

Base calling, quality value assignment, and vector trimming were performed with the assistance of PHRED/PHRAP software (University of Washington, Seattle, Wash., USA). Clustering analysis of the ESTs was performed with a Transcript Assembler v. 2.6.2. (Paracel, Inc., Pasadena, Calif., USA). Analysis of the EST clustering indicated the presence of 395 independent clusters.

Sequence homology analysis of the assembled EST sequences against databases was performed with the Blastx program (Altschul et. al., 1990, *J. Mol. Biol.* 215:403-410) on a 32-node Linux cluster (Paracel, Inc., Pasadena, Calif., USA) using the BLOSUM 62 matrix (Henikoff, 1992, *Proc. Natl. Acad. Sci. USA* 89: 10915-10919).

Example 4

Identification of cDNA Clones Encoding a *Thielavia terrestris* Serine Carboxypeptidase A cDNA clone encoding a *Thielavia terrestris* serine carboxypeptidase was initially identified by sequence homology to a characterized KEX1 carboxypeptidase from *Saccharomyces cerevisiae* (Cooper et al., 1989, *Mol. Cell. Biol.* 9: 2706-2714; UniProt accession number P09620).

After this initial identification, the clone, designated Tter44C2, was retrieved from the original frozen stock plate and streaked onto a LB plate supplemented with 50 µg of kanamycin per ml. The plate was incubated overnight at 37° C. and the next day a single colony from the plate was used to inoculate 3 ml of LB medium supplemented with 150 µg of kanamycin per ml. The liquid culture was incubated overnight at 37° C. and plasmid DNA was prepared using a BIOROBOT® 9600 (QIAGEN, Inc., Valencia, Calif., USA). Using a primer walking strategy, the inserted cDNA in the Tter44C2 plasmid was completely sequenced.

Analysis of the deduced protein sequence of Tter44C2 with the Interproscan program (Zdobnov and Apweiler, 2001, *Bioinformatics* 17: 847-8) showed that the gene encoded by Tter44C2 contained the Serine Protease Family S10 Serine Carboxypeptidase domain sequence signature known as the PF00450. This sequence signature is located at amino acids position 44 through 467 in the deduced peptide sequence (SEQ ID NO: 2).

The cDNA sequence (SEQ ID NO: 1) and deduced amino acid sequence (SEQ ID NO: 2) of the *Thielavia terrestris* serine carboxypeptidase gene are shown in FIGS. 1A and 1B. The cDNA clone encodes a polypeptide of 645 amino acids. The % G+C content of the coding sequence of the gene is 63.6% and of the mature protein coding region (nucleotides 263 to 2104 of SEQ ID NO: 1) is 63.2%. Using the SignalP software program (Nielsen et al., 1997, *Protein Engineering* 10:1-6), a signal peptide of 31 residues was predicted. The predicted mature protein contains 614 amino acids with a molecular mass of 68.6 kDa.

A comparative pairwise global alignment of amino acid sequences was determined using the Needleman-Wunsch algorithm (Needleman and Wunsch, 1970, *J. Mol. Biol.* 48: 443-453) as implemented in the Needle program of EMBOSS with a gap open penalty of 10, gap extension penalty of 0.5, and the EBLOSUM62 matrix. The alignment showed that the deduced amino acid sequence of the *Thielavia terrestris* carboxypeptidase gene shared 79.6% identity (excluding gaps) to the deduced amino acid sequences of putative uncharacterized protein (Uniprot accession number Q2GYB7) from *Chaetomium globosum* strain CBS 148.51 and a 35% identity to a characterized carboxypeptidase KEX1 *Saccharomyces cerevisiae* (Cooper et al., 1989, *Mol. Cell. Biol.* 9: 2706-2714; UniProt accession number P09620).

Once the identity of Tter44C2 was confirmed, a 0.5 μl aliquot of plasmid DNA from this clone (pTter44C2, FIG. 2) was transferred into a vial of *E. coli* TOP10 cells (Invitrogen Corp., Carlsbad, Calif., USA), gently mixed, and incubated on ice for 10 minutes. The cells were then heat-shocked at 42° C. for 30 seconds and incubated again on ice for 2 minutes. The cells were resuspended in 250 μl of SOC medium and incubated at 37° C. for 60 minutes with constant shaking at 200 rpm. After the incubation period, two 30 μl aliquots were plated onto LB plates supplemented with 50 μg of kanamycin per ml and incubated overnight at 37° C. The next day a single colony was picked and streaked onto three 1.8 ml cryovials containing about 1.5 ml of LB agarose supplemented with 50 μg of kanamycin per ml. The vials were sealed with PET-RISEAL™ (Diversified Biotech, Boston Mass., USA) and deposited with the Agricultural Research Service Patent Culture Collection, Northern Regional Research Center, Peoria, Ill., USA, as NRRL B-50207, with a deposit date of Dec. 11, 2008.

Deposit of Biological Material

The following biological material has been deposited under the terms of the Budapest Treaty with the Agricultural Research Service Patent Culture Collection (NRRL), Northern Regional Research Center, 1815 University Street, Peoria, Ill., USA, and given the following accession number:

| Deposit | Accession Number | Date of Deposit |
| --- | --- | --- |
| *E. coli* pTter44C2 | NRRL B-50207 | Dec. 11, 2008 |

The strain has been deposited under conditions that assure that access to the culture will be available during the pendency of this patent application to one determined by foreign patent laws to be entitled thereto. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The present invention is further described by the following numbered paragraphs:

[1] An isolated polypeptide having carboxypeptidase activity, selected from the group consisting of: (a) a polypeptide comprising an amino acid sequence having at least 80% sequence identity to the mature polypeptide of SEQ ID NO: 2; (b) a polypeptide encoded by a polynucleotide that hybridizes under at least high stringency conditions with (i) the mature polypeptide coding sequence of SEQ ID NO: 1, (ii) the genomic DNA sequence comprising the mature polypeptide coding sequence of SEQ ID NO: 1, or (iii) a full-length complementary strand of (i) or (ii); (c) a polypeptide encoded by a polynucleotide comprising a nucleotide sequence having at least 80% sequence identity to the mature polypeptide coding sequence of SEQ ID NO: 1; and (d) a variant comprising a substitution, deletion, and/or insertion of one or more (several) amino acids of the mature polypeptide of SEQ ID NO: 2.

[2] The polypeptide of paragraph 1, comprising an amino acid sequence having at least 80% sequence identity to the mature polypeptide of SEQ ID NO: 2.

[3] The polypeptide of paragraph 2, comprising an amino acid sequence having at least 85% sequence identity to the mature polypeptide of SEQ ID NO: 2.

[4] The polypeptide of paragraph 3, comprising an amino acid sequence having at least 90% sequence identity to the mature polypeptide of SEQ ID NO: 2.

[5] The polypeptide of paragraph 4, comprising an amino acid sequence having at least 95% sequence identity to the mature polypeptide of SEQ ID NO: 2.

[6] The polypeptide of paragraph 5, comprising an amino acid sequence having at least 97% sequence identity to the mature polypeptide of SEQ ID NO: 2.

[7] The polypeptide of paragraph 1, comprising or consisting of the amino acid sequence of SEQ ID NO: 2; or a fragment thereof having carboxypeptidase activity.

[8] The polypeptide of paragraph 7, comprising or consisting of the amino acid sequence of SEQ ID NO: 2.

[9] The polypeptide of paragraph 1, comprising or consisting of the mature polypeptide of SEQ ID NO: 2.

[10] The polypeptide of paragraph 1, which is encoded by a polynucleotide that hybridizes under at least high stringency conditions with (i) the mature polypeptide coding sequence of SEQ ID NO: 1, (ii) the genomic DNA sequence comprising the mature polypeptide coding sequence of SEQ ID NO: 1, or (iii) a full-length complementary strand of (i) or (ii).

[11] The polypeptide of paragraph 10, which is encoded by a polynucleotide that hybridizes under at least very high stringency conditions with (i) the mature polypeptide coding sequence of SEQ ID NO: 1, (ii) the genomic DNA sequence comprising the mature polypeptide coding sequence of SEQ ID NO: 1, or (iii) a full-length complementary strand of (i) or (ii).

[12] The polypeptide of paragraph 1, which is encoded by a polynucleotide comprising a nucleotide sequence having at least 80% sequence identity to the mature polypeptide coding sequence of SEQ ID NO: 1.

[13] The polypeptide of paragraph 12, which is encoded by a polynucleotide comprising a nucleotide sequence having at least 85% sequence identity to the mature polypeptide coding sequence of SEQ ID NO: 1.

[14] The polypeptide of paragraph 13, which is encoded by a polynucleotide comprising a nucleotide sequence having at least 90% sequence identity to the mature polypeptide coding sequence of SEQ ID NO: 1.

[15] The polypeptide of paragraph 14, which is encoded by a polynucleotide comprising a nucleotide sequence having at least 95% sequence identity to the mature polypeptide coding sequence of SEQ ID NO: 1.

[16] The polypeptide of paragraph 15, which is encoded by a polynucleotide comprising a nucleotide sequence having at least 97% sequence identity to the mature polypeptide coding sequence of SEQ ID NO: 1.

[17] The polypeptide of paragraph 1, which is encoded by a polynucleotide comprising or consisting of the nucleotide sequence of SEQ ID NO: 1; or a subsequence thereof encoding a fragment having carboxypeptidase activity.

[18] The polypeptide of paragraph 17, which is encoded by a polynucleotide comprising or consisting of the nucleotide sequence of SEQ ID NO: 1.

[19] The polypeptide of paragraph 1, which is encoded by a polynucleotide comprising or consisting of the mature polypeptide coding sequence of SEQ ID NO: 1.

[20] The polypeptide of paragraph 1, wherein the polypeptide is a variant comprising a substitution, deletion, and/or insertion of one or more (several) amino acids of the mature polypeptide of SEQ ID NO: 2.

[21] The polypeptide of paragraph 1, which is encoded by the polynucleotide contained in plasmid pTter44C2 which is contained in E. coli NRRL B-50207.

[22] The polypeptide of any of paragraphs 1-21, wherein the mature polypeptide is amino acids 32 to 645 of SEQ ID NO: 2.

[23] The polypeptide of any of paragraphs 1-22, wherein the mature polypeptide coding sequence is nucleotides 263 to 2104 of SEQ ID NO: 1.

[24] An isolated polynucleotide comprising a nucleotide sequence that encodes the polypeptide of any of paragraphs 1-23.

[25] The isolated polynucleotide of paragraph 24, comprising at least one mutation in the mature polypeptide coding sequence of SEQ ID NO: 1, in which the mutant nucleotide sequence encodes the mature polypeptide of SEQ ID NO: 2.

[26] A nucleic acid construct comprising the polynucleotide of paragraph 24 or 25 operably linked to one or more (several) control sequences that direct the production of the polypeptide in an expression host.

[27] A recombinant expression vector comprising the polynucleotide of paragraph 24 or 25.

[28] A recombinant host cell comprising the polynucleotide of paragraph 24 or 25 operably linked to one or more (several) control sequences that direct the production of a polypeptide having carboxypeptidase activity.

[29] A method of producing the polypeptide of any of paragraphs 1-23, comprising: (a) cultivating a cell, which in its wild-type form produces the polypeptide, under conditions conducive for production of the polypeptide; and (b) recovering the polypeptide.

[30] A method of producing the polypeptide of any of paragraphs 1-23, comprising: (a) cultivating a host cell comprising a nucleic acid construct comprising a nucleotide sequence encoding the polypeptide under conditions conducive for production of the polypeptide; and (b) recovering the polypeptide.

[31] A method of producing a mutant of a parent cell, comprising disrupting or deleting a polynucleotide encoding the polypeptide, or a portion thereof, of any of paragraphs 1-23, which results in the mutant producing less of the polypeptide than the parent cell.

[32] A mutant cell produced by the method of paragraph 31.

[33] The mutant cell of paragraph 32, further comprising a gene encoding a native or heterologous protein.

[34] A method of producing a protein, comprising: (a) cultivating the mutant cell of paragraph 33 under conditions conducive for production of the protein; and (b) recovering the protein.

[35] The isolated polynucleotide of paragraph 24 or 25, obtained by (a) hybridizing a population of DNA under at least high stringency conditions with (i) the mature polypeptide coding sequence of SEQ ID NO: 1, (ii) the genomic DNA sequence comprising the mature polypeptide coding sequence of SEQ ID NO: 1, or (iii) a full-length complementary strand of (i) or (ii); and (b) isolating the hybridizing polynucleotide, which encodes a polypeptide having carboxypeptidase activity.

[36] The isolated polynucleotide of paragraph 35, obtained by (a) hybridizing a population of DNA under at least very high stringency conditions with (i) the mature polypeptide coding sequence of SEQ ID NO: 1, (ii) the genomic DNA sequence comprising the mature polypeptide coding sequence of SEQ ID NO: 1, or (iii) a full-length complementary strand of (i) or (ii); and (b) isolating the hybridizing polynucleotide, which encodes a polypeptide having carboxypeptidase activity.

[37] The isolated polynucleotide of paragraph 33 or 34, wherein the mature polypeptide coding sequence is nucleotides 263 to 2104 of SEQ ID NO: 1.

[38] A method of producing a polynucleotide comprising a mutant nucleotide sequence encoding a polypeptide having carboxypeptidase activity, comprising: (a) introducing at least one mutation into the mature polypeptide coding sequence of SEQ ID NO: 1, wherein the mutant nucleotide sequence encodes a polypeptide comprising or consisting of the mature polypeptide of SEQ ID NO: 2; and (b) recovering the polynucleotide comprising the mutant nucleotide sequence.

[39] A mutant polynucleotide produced by the method of paragraph 38.

[40] A method of producing a polypeptide, comprising: (a) cultivating a cell comprising the mutant polynucleotide of paragraph 39 encoding the polypeptide under conditions conducive for production of the polypeptide; and (b) recovering the polypeptide.

[41] A method of producing the polypeptide of any of paragraphs 1-23, comprising: (a) cultivating a transgenic plant or a plant cell comprising a polynucleotide encoding the polypeptide under conditions conducive for production of the polypeptide; and (b) recovering the polypeptide.

[42] A transgenic plant, plant part or plant cell transformed with a polynucleotide encoding the polypeptide of any of paragraphs 1-23.

[43] A double-stranded inhibitory RNA (dsRNA) molecule comprising a subsequence of the polynucleotide of paragraph 24 or 25, wherein optionally the dsRNA is a siRNA or a miRNA molecule.

[44] The double-stranded inhibitory RNA (dsRNA) molecule of paragraph 43, which is about 15, 16, 17, 18, 19, 20, 21, 22, 23, 24, 25 or more duplex nucleotides in length.

[45] A method of inhibiting the expression of a polypeptide having carboxypeptidase activity in a cell, comprising administering to the cell or expressing in the cell a double-stranded RNA (dsRNA) molecule, wherein the dsRNA comprises a subsequence of the polynucleotide of paragraph 24 or 25.

[46] The method of paragraph 45, wherein the dsRNA is about 15, 16, 17, 18, 19, 20, 21, 22, 23, 24, 25 or more duplex nucleotides in length.

[47] An isolated polynucleotide encoding a signal peptide comprising or consisting of amino acids 1 to 31 of SEQ ID NO: 2.

[48] A nucleic acid construct comprising a gene encoding a protein operably linked to the polynucleotide of paragraph 47, wherein the gene is foreign to the polynucleotide encoding the signal peptide.

[49] A recombinant expression vector comprising a gene encoding a protein operably linked to the polynucleotide of paragraph 47, wherein the gene is foreign to the polynucleotide encoding the signal peptide.

[50] A recombinant host cell comprising a gene encoding a protein operably linked to the polynucleotide of paragraph 47, wherein the gene is foreign to the polynucleotide encoding the signal peptide.

[51] A method of producing a protein, comprising: (a) cultivating a recombinant host cell comprising a gene encoding a protein operably linked to the polynucleotide of paragraph 47, wherein the gene is foreign to the polynucleotide encoding the signal peptide, under conditions conducive for production of the protein; and (b) recovering the protein.

[52] A composition comprising the polypeptide of any of paragraphs 1-23.

[53] A method of producing a hydrolysate from a proteinaceous substrate which comprises subjecting the substrate to a polypeptide of any of paragraphs 1-23 and an endopeptidase.

[54] A protein hydrolysate produced by the method of paragraph 53.

[55] A food product comprising the protein hydrolysate of paragraph 54.

[56] A method of obtaining from a proteinaceous substrate a hydrolysate enriched in free glutamic acid and/or peptide bound glutamic acid residues, comprising subjecting the substrate to a deamidation process and a polypeptide of any of paragraphs 1-23.

[57] The method of paragraph 56, further comprising subjecting the substrate to one or more unspecific acting endo- and/or exo-peptidase enzymes.

[58] A protein hydrolysate obtained by the method of paragraph 56 or 57.

[69] A food product comprising the hydrolysate of paragraph 58.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. A method of producing a hydrolysate from a proteinaceous substrate which comprises subjecting the substrate to an endopeptidase and a polypeptide having carboxypeptidase activity, selected from the group consisting of:
   (a) a polypeptide comprising an amino acid sequence having at least 95% sequence identity to the mature polypeptide of SEQ ID NO: 2; and
   (b) a polypeptide encoded by a polynucleotide comprising a nucleotide sequence having at least 95% sequence identity to the mature polypeptide coding sequence of SEQ ID NO: 1;
   wherein said polypeptide has the carboxypeptidase activity of SEQ ID NO: 2.

2. The method of claim 1, wherein the polypeptide comprises the amino acid sequence of SEQ ID NO: 2 or the mature polypeptide thereof; or a fragment thereof having carboxypeptidase activity.

3. The method of claim 1, wherein the polypeptide is encoded by the polynucleotide contained in plasmid pTter44C2 which is contained in *E. coli* NRRL B-50207.

4. A method of obtaining from a proteinaceous substrate a hydrolysate enriched in free glutamic acid and/or peptide bound glutamic acid residues, comprising subjecting the substrate to a deamidation process and a polypeptide having carboxypeptidase activity, selected from the group consisting of:
   (a) a polypeptide comprising an amino acid sequence having at least 95% sequence identity to the mature polypeptide of SEQ ID NO: 2; and
   (b) a polypeptide encoded by a polynucleotide comprising a nucleotide sequence having at least 95% sequence identity to the mature polypeptide coding sequence of SEQ ID NO: 1; wherein said polypeptide has the carboxypeptidase activity of SEQ ID NO: 2.

5. The method of claim 4, wherein the polypeptide comprises the amino acid sequence of SEQ ID NO: 2 or the mature polypeptide thereof; or a fragment thereof having carboxypeptidase activity.

6. The method of claim 4, wherein the polypeptide is encoded by the polynucleotide contained in plasmid pTter44C2 which is contained in *E. coli* NRRL B-50207.

7. The method of claim 4, further comprising subjecting the substrate to one or more unspecific acting endo- and/or exopeptidase enzymes.

8. The method of claim 1, wherein the polypeptide comprises an amino acid sequence having at least 95% sequence identity to the mature polypeptide of SEQ ID NO: 2.

9. The method of claim 1, wherein the polypeptide comprises an amino acid sequence having at least 96% sequence identity to the mature polypeptide of SEQ ID NO: 2.

10. The method of claim 1, wherein the polypeptide comprises an amino acid sequence having at least 97% sequence identity to the mature polypeptide of SEQ ID NO: 2.

11. The method of claim 1, wherein the polypeptide comprises an amino acid sequence having at least 98% sequence identity to the mature polypeptide of SEQ ID NO: 2.

12. The method of claim 1, wherein the polypeptide comprises an amino acid sequence having at least 99% sequence identity to the mature polypeptide of SEQ ID NO: 2.

13. The method of claim 1, wherein the polypeptide is encoded by a polynucleotide comprising a nucleotide sequence having at least 95% sequence identity to the mature polypeptide coding sequence of SEQ ID NO: 1.

14. The method of claim 1, wherein the polypeptide is encoded by a polynucleotide comprising a nucleotide sequence having at least 96% sequence identity to the mature polypeptide coding sequence of SEQ ID NO: 1.

15. The method of claim 1, wherein the polypeptide is encoded by a polynucleotide comprising a nucleotide sequence having at least 97% sequence identity to the mature polypeptide coding sequence of SEQ ID NO: 1.

16. The method of claim 1, wherein the polypeptide is encoded by a polynucleotide comprising a nucleotide sequence having at least 98% sequence identity to the mature polypeptide coding sequence of SEQ ID NO: 1.

17. The method of claim 1, wherein the polypeptide is encoded by a polynucleotide comprising a nucleotide sequence having at least 99% sequence identity to the mature polypeptide coding sequence of SEQ ID NO: 1.

18. The method of claim 4, wherein the polypeptide comprises an amino acid sequence having at least 95% sequence identity to the mature polypeptide of SEQ ID NO: 2.

19. The method of claim 4, wherein the polypeptide comprises an amino acid sequence having at least 96% sequence identity to the mature polypeptide of SEQ ID NO: 2.

20. The method of claim 4, wherein the polypeptide comprises an amino acid sequence having at least 97% sequence identity to the mature polypeptide of SEQ ID NO: 2.

21. The method of claim 4, wherein the polypeptide comprises an amino acid sequence having at least 98% sequence identity to the mature polypeptide of SEQ ID NO: 2.

22. The method of claim 4, wherein the polypeptide comprises an amino acid sequence having at least 99% sequence identity to the mature polypeptide of SEQ ID NO: 2.

23. The method of claim 4, wherein the polypeptide is encoded by a polynucleotide comprising a nucleotide sequence having at least 95% sequence identity to the mature polypeptide coding sequence of SEQ ID NO: 1.

24. The method of claim 4, wherein the polypeptide is encoded by a polynucleotide comprising a nucleotide sequence having at least 96% sequence identity to the mature polypeptide coding sequence of SEQ ID NO: 1.

25. The method of claim 4, wherein the polypeptide is encoded by a polynucleotide comprising a nucleotide sequence having at least 97% sequence identity to the mature polypeptide coding sequence of SEQ ID NO: 1.

26. The method of claim 4, wherein the polypeptide is encoded by a polynucleotide comprising a nucleotide sequence having at least 98% sequence identity to the mature polypeptide coding sequence of SEQ ID NO: 1.

27. The method of claim 4, wherein the polypeptide is encoded by a polynucleotide comprising a nucleotide sequence having at least 99% sequence identity to the mature polypeptide coding sequence of SEQ ID NO: 1.

* * * * *